United States Patent
Tranah et al.

(10) Patent No.: US 11,332,792 B2
(45) Date of Patent: May 17, 2022

(54) MITOCHONDRIAL DNA MUTATION PROFILE FOR PREDICTING HUMAN HEALTH CONDITIONS AND DISEASE RISK AND FOR MONITORING TREATMENTS

(71) Applicant: Sutter West Bay Hospitals, San Francisco, CA (US)

(72) Inventors: Gregory J. Tranah, San Francisco, CA (US); Steven R. Cummings, Mill Valley, CA (US); Shana M. Katzman, San Francisco, CA (US)

(73) Assignee: SUTTER BAY HOSPITALS, San Francisco, CA (US)

( * ) Notice: Subject to any disclaimer, the term of this patent is extended or adjusted under 35 U.S.C. 154(b) by 616 days.

(21) Appl. No.: 15/329,855

(22) PCT Filed: Jul. 30, 2015

(86) PCT No.: PCT/US2015/042923
§ 371 (c)(1),
(2) Date: Jan. 27, 2017

(87) PCT Pub. No.: WO2016/019149
PCT Pub. Date: Feb. 4, 2016

(65) Prior Publication Data
US 2017/0268057 A1    Sep. 21, 2017

Related U.S. Application Data

(60) Provisional application No. 62/030,875, filed on Jul. 30, 2014.

(51) Int. Cl.
| | | |
|---|---|---|
| *C12Q 1/68* | (2018.01) | |
| *C12Q 1/6883* | (2018.01) | |
| *G16H 20/00* | (2018.01) | |
| *G16H 70/20* | (2018.01) | |
| *G16B 20/20* | (2019.01) | |
| *G16B 20/00* | (2019.01) | |
| *G16B 50/00* | (2019.01) | |
| *G16H 50/30* | (2018.01) | |

(52) U.S. Cl.
CPC .......... *C12Q 1/6883* (2013.01); *G16B 20/20* (2019.02); *G16H 20/00* (2018.01); *G16H 70/20* (2018.01); *C12Q 2600/106* (2013.01); *C12Q 2600/118* (2013.01); *C12Q 2600/156* (2013.01); *G16B 20/00* (2019.02); *G16B 50/00* (2019.02); *G16H 50/30* (2018.01)

(58) Field of Classification Search
None
See application file for complete search history.

(56) References Cited

U.S. PATENT DOCUMENTS

| | | |
|---|---|---|
| 5,494,794 A | 2/1996 | Wallace |
| 5,976,798 A | 11/1999 | Parker et al. |
| 2011/0105855 A1 | 5/2011 | Johnson |

OTHER PUBLICATIONS

Carelli et al; Neurology, vol. 48, pp. 1623-1632; 1997.*
Ambrosio et al; Documenta Opthalmologica; vol. 89, pp. 219-228, 1995.*
Simon et al; Neurology, vol. 53, pp. 1787-1793; 1999; pp. 1-13 from the internet.*
Piotrowska et al; Gene; vol. 555, pp. 41-49, published online Sep. 26, 2014.*
Singh (Pharmacy Practice, 2014, vol. 12:489).*
Crimi, Marco, et. al., "A New Mitochondrial DNA Mutation in ND3 Gene Causing Severe Leigh Syndrome with Early Lethality," Pediatric Research, May 2004, vol. 55, No. 5, pp. 842-846.
Young, Lee W., International Search Report and Written Opinion, International Application No. PCT/US2015/042923, dated Dec. 15, 2015.
Wittmann-Regis, Agnes., International Preliminary Report on Patentability and Written Opinion, International Application No. PCT/US2015/042923, dated Feb. 9, 2017.

* cited by examiner

*Primary Examiner* — Jehanne S Sitton
(74) *Attorney, Agent, or Firm* — Gavrilovich, Dodd & Lindsey LLP

(57) ABSTRACT

The disclosure provides methods, algorithms and compositions for determining the risk, diagnosis or prognosis of mitochondrial-associated disease and disorders by determining the mutational heteroplasmic burden in a subject.

3 Claims, 5 Drawing Sheets

MITOCHONDRIAL DNA MUTATION PROFILE FOR PREDICTING HUMAN HEALTH CONDITIONS AND DISEASE RISK AND FOR MONITORING TREATMENTS

CROSS REFERENCE TO RELATED APPLICATIONS

This application is a U.S. National Stage Application filed under 35 U.S.C. § 371 and claims priority to International Application No. PCT/US2015/042923, filed Jul. 30, 2015, which application claims priority under 35 U.S.C. § 119 from Provisional Application Ser. No. 62/030,875, filed Jul. 30, 2014, the disclosures of which are incorporated herein by reference.

TECHNICAL FIELD

The disclosure relates to methods, algorithms and compositions for determining disease risk based upon mitochondrial heteroplasmy.

BACKGROUND

The mammalian mitochondrial genome (mtDNA) is a double-stranded DNA molecule that is transmitted through the maternal line. The human mitochondrial DNA is a ringed two-chain molecule consisting of 16,569 nucleotide pairs that encode 37 genes. Twenty-two genes encode transport RNAs (tRNAs), 2 genes encode ribosomal RNAs (rRNAs), and 13 genes encode subunits of the respiration chain complex such as cytochrome B, ATPase, cytochrome-C-oxidase, and NADH-dehydrogenase. A mitochondrion usually contains multiple copies of its genome. The maternally inherited mitochondrial genome is characteristically unstable; thus, the occurrence of somatic mutations during the life of an individual is common. The penetrance and expressivity of such mutations vary widely between families, and between relatives (in the maternal line) within a family. Although many factors influence penetrance and expressivity, two main factors are genotype and the level of heteroplasmy (mixture of mutant and normal DNA molecules).

Heteroplasmy is defined as the presence of a mixture of more than one type of an organellar genome within a cell or individual. Pathogenic mtDNA mutations are usually heteroplasmic, with a mixture of mutant and wild-type mtDNA within the same organism. A woman harboring one of these mutations transmits a variable amount of mutant mtDNA to each offspring.

SUMMARY

Inheritance and penetrance of mtDNA mutations is not Mendelian, but rather depends on the relative amount (%) of wild-type and mutant mtDNA molecules per cell. The normal state is 100% wild-type mtDNA or wild-type homoplasmy. A mutation in mtDNA can also be homoplasmic (present in all mtDNA molecules of a cell) in which case it is likely to have a functional and possibly pathogenic effect. The presence of a mixture of mutant and wild-type mtDNA molecules in an individual cell is referred to as heteroplasmy. Because normal cells have an excess capacity of mtDNA and mtDNA-encoded proteins, heteroplasmic mutant mtDNA are believed to cause an altered functional (or pathogenic) phenotype if the mutant mtDNAs are present at levels exceeding some threshold value, usually 70-90%.

An additional consequence of heteroplasmy is the development of altered functions of mitochondria within a single cell, between cells and between tissues.

Heteroplasmy has been associated with aging and disease in humans. The vast majority of deleterious mtDNA point mutations are heteroplasmic and their mutant load can vary significantly among different tissues, even in the same subject. Heteroplasmic mtDNA defects are considered an important cause of human disease with clinical features that primarily involve nondividing (postmitotic) tissues. The proportion of mutant out of total mtDNA in a cell, called the heteroplasmy level, is an important factor in determining the amount of mitochondrial dysfunction and therefore the disease severity.

The disclosure provides a panel of mtDNA mutations that are useful in predicting human health conditions and disease risk, and can be used for monitoring treatments. The disclosure describes strong associations between numerous mtDNA mutations and human health conditions and disease risk. The mtDNA health panel will include both known mtDNA mutations that have been demonstrated to cause inherited diseases and novel mtDNA discoveries made in the course of the studies described herein.

The disclosure provides a method of determining a risk of a clinically relevant cognitive decline comprising: (a) isolating mtDNA; (b) measuring a heteroplasmy at 10158 of the mtDNA; (c) determining the frequency of 10158T compared to 10158C; wherein when the frequency of 10158C is greater than 10% of the total number of alleles (10158C+10158T) then the subject is at risk for clinically significant cognitive decline as measured by the Modified Mini-Mental State Examination.

The disclosure also provides a method of determining a risk of a clinically relevant vision loss comprising: (a) isolating mtDNA; (b) measuring a heteroplasmy at 11778 of the mtDNA; (c) determining the frequency of 11778A compared to 11778G; wherein when the frequency of 11778A is greater than 9.5% of the total number of alleles (11778A+11778G) then the subject is at risk for clinically significant vision loss as measured by contrast sensitivity testing.

The disclosure also provides a method of determining a risk of a clinically relevant mobility decline comprising: (a) isolating mtDNA; (b) measuring a heteroplasmy at 5703 of the mtDNA; (c) determining the frequency of 5703A compared to 5703G; wherein when the frequency of 5703A is greater than 11% of the total number of alleles (5703A+5703G) then the subject is at risk for clinically significant mobility decline as measured by 400 m walking speed.

The disclosure provides a method of determining a risk of a clinically relevant hearing loss comprising: (a) isolating mtDNA; (b) measuring a heteroplasmy at 7445 of the mtDNA; (c) determining the frequency of 7445A compared to 7445G; wherein when the frequency of 7445A is greater than 25% of the total number of alleles (7445A+7445G) then the subject is at risk for clinically significant high frequency hearing loss as measured by high frequency hearing testing.

The disclosure provides a method of determining a risk of a clinically relevant cognitive decline that includes a) isolating mtDNA from a tissue sample; (b) determining the presence and frequency of at least one mutation in a nucleic acid sequence encoding at least one subunit of mitochondrial complex I, wherein the presence of at least one mutation correlates with risk of clinically relevant cognitive decline; (c) quantitiating the degree of heteroplasmy at the site of the at least one mutation; and (d) correlating the presence of the at least one mutation and the degree of heteroplasmy with the risk of having clinically relevant cognitive decline.

The disclosure further provides a method of predicting a human subjects predisposition for developing a mitochondrial-associated disease, the method including (a) determining the presence and frequency of at least one mutation in a nucleic acid sequence encoding at least one subunit of mitochondrial complex I; (b) determining the degree of heteroplasmy at the site of the at least one mutation; (c) correlating the presence of the at least one mutation and the degree of heteroplasmy with at least one additional risk factor indicative of a mitochondrial-associated disease. In general the presence of increased heteroplasmy at the site of the at least one mutation, and the presence of at least one risk factor associated with a mitochondrial-associated disease correlates with an increased likelihood of the human subject developing the mitochondrial-associated disease.

In some aspects the disclosure provides mitochondrial mutations in a nucleic acid sequence encoding at least one subunit of mitochondrial complex I. Such mutations include, but are not limited to, m.10158T>C, m.10191T>C, m.10197G>A, m.13091T>C, m.13513G>A, m.13514A>G, m.14487T>C, m.15244A>G, m.5046G>A, m.1703C>T, m.2850C>T, m.2639C>T, m.3915G>A, m.10589G>A, m.15758A>G, m.6776T>C, m.3918G>A, m.6152T>C, m.11899T>C, m.11778G>A, and m.15244A>G.

The disclosure further provides a method of determining a treatment plan for a subject predisposed for developing a mitochondrial-associated disease. The method includes (a) determining the presence and frequency of at least one mutation in a nucleic acid sequence encoding at least one subunit of mitochondrial complex I; (b) determining the degree of heteroplasmy at the site of the at least one mutation; (c) correlating the presence of the at least one mutation and the degree of heteroplasmy with at least one additional risk factor indicative of a mitochondrial-associated disease. In general the presence of increased heteroplasmy at the site of the at least one mutation, and the presence of at least one risk factor associated with a mitochondrial-associated disease correlates with an increased likelihood of the human subject developing the mitochondrial-associated disease. Such methods further include generating a risk assessment based on the correlation and devising a treatment plan based on the risk assessment. The treatment plan can be generated from a treatment protocol database that is populated with one or more treatment protocols that provide guidelines for treating patients with the correlation.

The disclosure provides a system for generating a treatment protocol for a subject having, or predisposed for developing, a mitochondrial-associated disease. The system includes: (a) a processor; (b) a patient database that receives patient data from a treating provider. The patient data includes: (i) identification of the presence and frequency of at least one mutation in a nucleic acid sequence encoding at least one subunit of mitochondrial complex in a biological sample comprising mitochondria obtained from the patient; (ii) identification of the degree of heteroplasmy at the site of the at least one mutation in a biological sample comprising mitochondria obtained from the patient; (iii) a correlation of the presence of the at least one mutation and the degree of heteroplasmy with at least one risk factor indicative of a mitochondrial-associated disease, wherein the correlation is indicative of increased likelihood of a negative clinical outcome. The system further includes (c) a treatment protocol database that is populated with one or more treatment protocols that provide guidelines for treating patients with the correlation of b), iii) above. The system includes a means for determining a treatment protocol.

The disclosure further discloses a computer system for generating a personalized health plan that includes: (a) a database comprising a mitochondrial genomic profile of a subject; (b) a processor for: (i) determining the degree of heteroplasmy for at least one nucleotide position of the mitochondrial genome of the subject based on the database of (a); (ii) correlating the degree of heteroplasmy of (b) (i) with the risk of having a clinically relevant mitochondrial-associated disease or condition; (iii) optionally correlating the degree of heteroplasmy determined in (b) (i), and the risk of having a clinically relevant mitochondrial-associated disease or condition in (b) (ii), with at least one additional phenotypic characteristic of the subject; and (iv) generating a personalized health plan based on (b) (i), (ii), and (iii). The computer system includes (c) a means for outputting the personalized health plan to the subject or health care manager of the subject. The personalized health plan optionally includes a recommendation(s) for alleviating the symptoms associated with clinically relevant mitochondrial-associated disease or condition.

In any of the foregoing, the mtDNA is isolated from a mitotic or postmitotic cell population. In a further embodiment, the postmitotic cell population comprises platelet cells. In another embodiment, the mtDNA is obtain from blood. In yet another embodiment, the mtDNA is obtain from a tissue selected from the group consisting of muscle, brain, skin, liver, kidney, urogenital and intestine.

DETAILED DESCRIPTION

Figure 1:
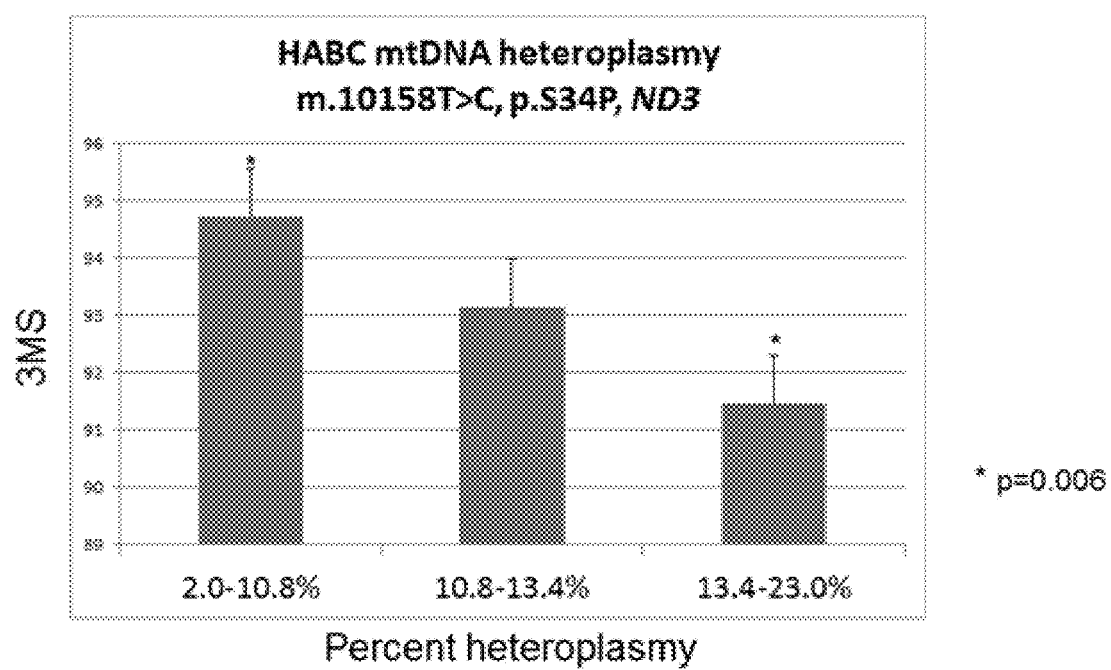
FIG. 1 shows mitochondrial m.10158T>C, p.S34P, ND3 association with year three Modified Mini-Mental State Examination (3MS, linear regression p=0.009). Year three 3MS was compared across tertiles of heteroplasmy (n=44 per group). Values adjusted for age, sex, and year one 3MS score.
Figure 2:
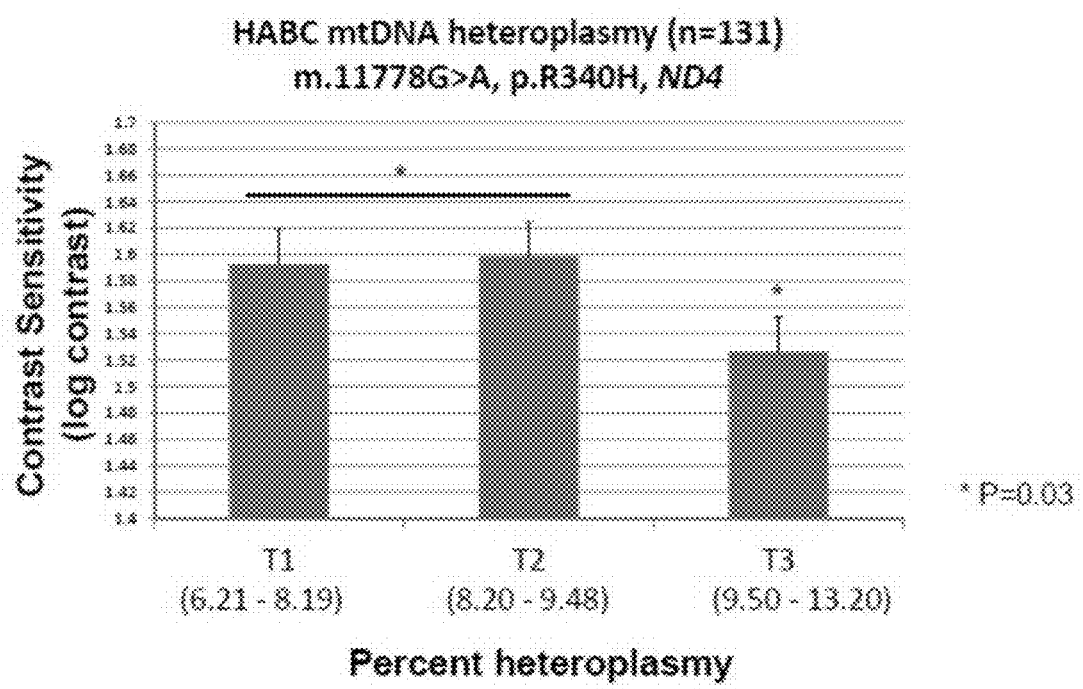
FIG. 2 shows mitochondrial m.11778G>A, heteroplasmy and vision loss.
Figure 3:
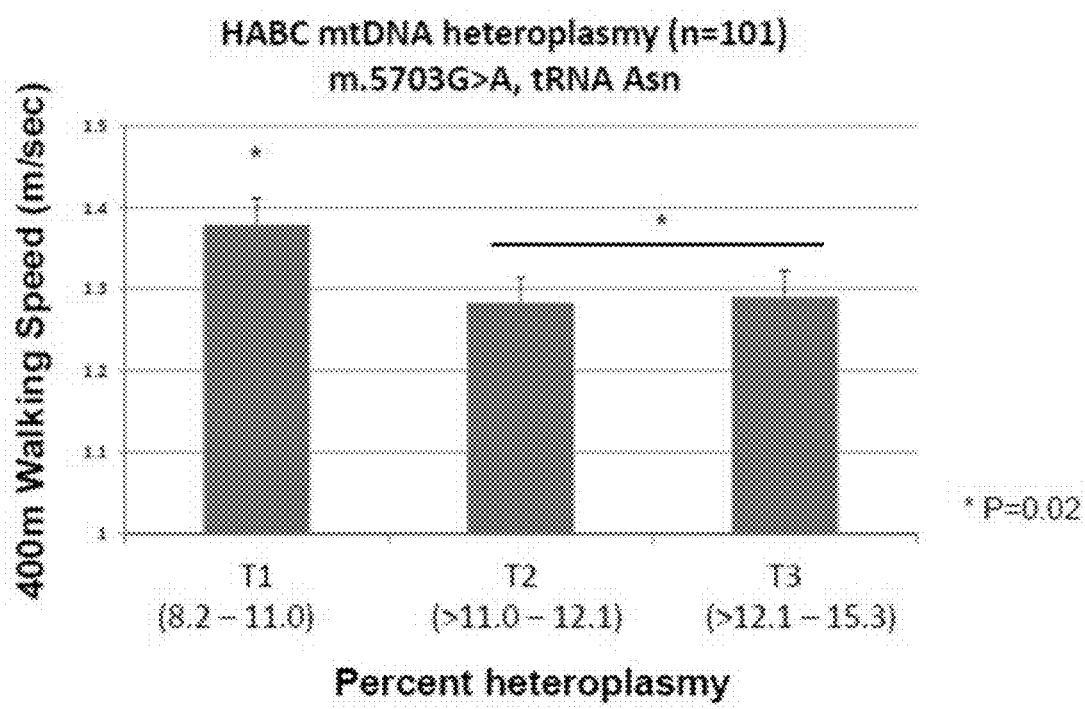
FIG. 3 shows mitochondrial m.5703G>A, heteroplasmy and mobility loss.
Figure 4:
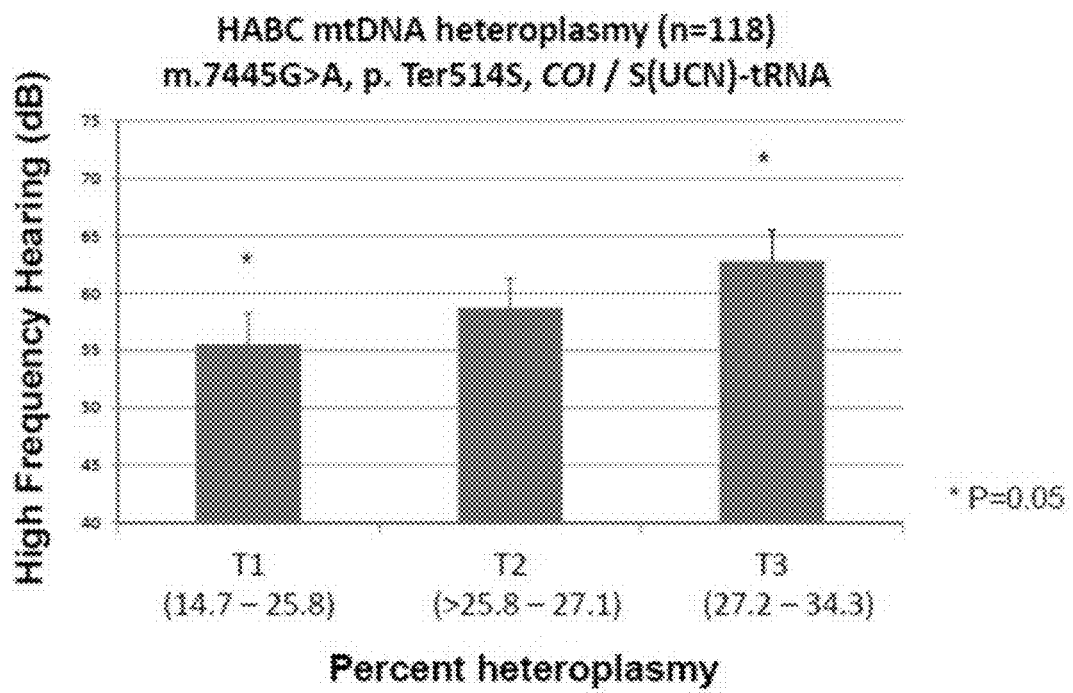
FIG. 4 shows mitochondrial m.7445G>A, heteroplasmy and hearing loss.

As used herein and in the appended claims, the singular forms "a," "and," and "the" include plural referents unless the context clearly dictates otherwise. Thus, for example, reference to "a nucleic acid" includes a plurality of such nucleic acids and reference to "the mutation" includes reference to one or more mutations and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in their entirety for the purposes of describing and disclosing methodologies, which are described in the publications that might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Low level mtDNA heteroplasmy, a mixture of normal and mutant mtDNA molecules in the cell, is common and often inherited in humans. Elevated heteroplasmy levels have been reported in various tissues of elderly individuals and large-scale mtDNA deletions increase with age in skeletal muscle, heart, brain and central nervous system. Age-related somatic mtDNA mutations accumulate in postmitotic tissues until a tissue-specific threshold in the ratio of mutant to normal mtDNA molecules is surpassed and cells become compromised energetically. The human brain is particularly susceptible to defective mitochondrial function resulting from heteroplasmic mtDNA mutations as acquired mtDNA deletions and base substitutions lead to OXPHOS defects.

Bioenergetic defects resulting from acquired and inherited mtDNA mutations lead to brain malformations and are critical for both age-related dementia and associated neuropathological changes observed in AD. OXPHOS enzyme activities decline with age in the human brain and this decline is correlated with the accumulation of somatic mtDNA deletions and base substitutions. Organ-specific analysis of brain aging has revealed a progressive decline in mitochondrial gene expression in rats, rhesus macaques and humans. These early alterations to mitochondria, which induce multiple abnormalities, may present more desirable therapeutic targets than the reversal of the individual pathologies occurring later in the disease process.

Nearly every inherited mitochondrial disease resulting from specific mtDNA deletions or mutations is accompanied by significant neurological impairments. MRI abnormalities have been reported in patients with mitochondrial respiratory chain disorders and a common pattern of brain MRI imaging was recently identified among patients with seven specific mtDNA mutations that lead to complex I deficiency (m.10158T>C, m.10191T>C, m.10197G>A, m.13091T>C, m.13513G>A, m.13514A>G, m.14487T>C). The common MRI patterns related to these seven complex I mutations included abnormal signal intensities in the brainstem and subtentorial nuclei, bilateral brainstem lesions, and anomalies of the putamen. Complex I deficiency is the most frequent cause of respiratory chain defects and accounts for a large number of rare clinical presentations including lactic acidosis and stroke-like episodes (MELAS), Leber hereditary optic neuropathy (LHON), mitochondrial encephalomyopathy, Leigh syndrome, hypotonia, seizures, cardiomyopathy, and retinopathy. To date, mtDNA heteroplasmy at these disease-causing sites has not been examined for impacts on cognitive aging. In the present study platelet heteroplasmy at these seven pathogenic mtDNA sites was examined to identify novel associations with cognitive function in the elderly. Platelets also constitute a good peripheral model to examine the metabolism of amyloid precursor protein (APP) and the early pathogenic events in the neurodegenerative process. Identifying peripheral markers of mtDNA heteroplasmy associated with increased risk of age-related cognitive decline may yield widely applicable and inexpensive biomarkers that could be used to identify persons in the early stages of neurodegeneration and who may benefit from existing pharmacologic and behavioral treatments that target mitochondria.

The panel of mtDNA mutations (heteroplasmy), which are acquired over the lifespan of a subject, impact health conditions and disease risk. These mtDNA mutation levels can be used to track interventions (pharmaceutical or behavioral) that target mitochondria.

The disclosure provides methods of prediction and analysis of heteroplasmy that are different from existing genetic tests as it examines acquired changes in mtDNA mutations (heteroplasmy that accumulates with age) and is not based on inherited polymorphisms that other services provide. The dataset of the disclosure links mtDNA heteroplasmy and human health conditions and disease risk. Several associations between increased levels of mtDNA mutations and health conditions are provided and are in the additional links are being expanded based upon the data analysis, methods and compositions provided herein.

Low-level mtDNA heteroplasmy in humans is common and may originate in early development or even in the germline despite protective mechanisms that minimize the maternal transmission of mutated mtDNA. Whether this early-life mutation load is the result of maternally transmitted mtDNA mutations or is acquired during a critical period in childhood or early adult life remains uncertain. Nevertheless, this pre-existing mutation load may provide a baseline upon which somatic mutagenesis acts over an individual's lifetime leading to the expansion of individual mtDNA point mutations. Heteroplasmic mutations and rearrangements of mtDNA have been reported in various tissues of elderly individuals and large-scale mtDNA deletions increase with age in skeletal muscle, heart, brain and central nervous system. The age-related accumulation of mtDNA mutations leads to impaired capacity for energy generation by OXPHOS, decreased cellular stress resistance, and accelerated cellular mortality. Moreover, elderly adults develop more mtDNA damage and exhibit reduced activity of OXPHOS enzymes in postmitotic tissues compared to young and middle aged adults. In general, organs with the highest ATP requirements and the lowest regenerative capacities, such as the brain, heart and skeletal muscle, are the most sensitive to the effects of mtDNA mutations. Several conserved mechanisms underlie the changes observed in the aging brain and considerable evidence suggests that altered mitochondrial function precedes plaques, tangles and clinical manifestations of Alzheimer's disease (AD) in humans. Identifying circulating mtDNA markers related to early cognitive impairment may lead to the development of widely applicable and inexpensive biomarkers that could be used to identify persons in the early stages of neurodegeneration. To date, this area of inquiry has been understudied and is represented by relatively small and underpowered studies of end stage AD. In the present study seven mtDNA complex I mutations previously linked to brain MRI abnormalities and identified a highly significant association between platelet-derived m.10158T>C heteroplasmy and 3MS score were analyzed.

The frequency of heteroplasmic variants can vary considerably among different tissues of the same individual. Carriers of the pathogenic m.10158T>C mutation exhibit variable tissue heteroplasmy in muscle (>80%), fibroblasts (>80%), and blood (48%) and experience severe complex I deficiency in muscle and fibroblasts. The high m.10158T>C mutation levels in the probands and absence from the patients' parents or maternal relatives suggests that these are de novo mutations. The m.10158T>C, p.S34P, ND3 substitution is one of three pathogenic Leigh syndrome mutations that have been identified in a 15 amino acid mutational hotspot located in the extramembrane loop connecting two putative transmembrane helices of ND3. The location of these disease-causing mutations suggests that this domain interacts with other mitochondrial and nuclear encoded complex I subunits and may affect overall assembly or structural stability. At the protein level. The m.10158T>C, p.S34P, ND3 substitution results in moderately reduced amounts (44-65%) of fully assembled complex I in fibroblasts from mutation carriers. The drastic reduction in complex I activity was observed in both muscle (85% reduction) and fibroblasts (89% reduction) from m.10158T>C mutation carriers support a stronger role for the mutation in catalysis rather than complex I assembly or stability. Interestingly, McFarland et al. constructed cybrids derived from fibroblasts of m.10158T>C mutation carriers and demonstrated that residual complex I enzyme activity was inversely related to the load of the mutant allele. No cybrids were obtained with less than 44% m.10158T>C mutant load suggesting that mutant loads of at least 40% lead to a complex I defect. It is unclear if these results represent a threshold effect or a linear relationship at lower m.10158T>C mutant loads like those observed in the present study (2-23%).

The extent to which lower levels of mtDNA heteroplasmy contribute to aging and declining function, though, remains unclear and the mechanism leading to the unequal partitioning of mitochondrial genotypes within and among individual cells is unknown and varies by cell type. Given that mtDNA heteroplasmy is development, tissue, and cell specific, characterizing when and where somatic mutations occur will have important implications for understanding pathogenesis. For example, a heteroplasmic cell containing predominantly mutant mtDNA may be less likely to maintain membrane potential and more likely to produce elevated ROS, increasing the probability that it will be targeted for removal through mitophagy. By contrast, the clonal expansion of mtDNA point mutations during human life could also be enhanced by a replicative advantage for specific mutation types; however, this positive selection is not essential for the accumulation of mtDNA mutations. Indeed, the continuous destruction and copying of mtDNA over many decades can lead to dramatic changes in the percentage level of mutant mtDNA in non-dividing cells through random genetic drift. This age-related accumulation of somatic mtDNA mutations in postmitotic tissues has been shown to continue until a certain tissue-specific threshold of mutant mtDNA molecules is surpassed and cells become energetically compromised. The differing mutation patterns observed in post mitotic and dividing cells (e.g. blood) may result from different rates of cell and mtDNA turnover between tissues. As previously discussed, the loss of mutations is much less likely in a post mitotic tissue where the replication of mtDNA can lead to an increase in mutation load during life within individual cells and the tissue as a whole, even from very low levels of heteroplasmy. By contrast, rapid turnover of blood cells could lead to the partial or complete loss of acquired mtDNA mutations observed in post mitotic tissues, either through selection against a particular mutation or genetic drift.

To determine mutation load and disease/disorder correlation the described study sequenced the mtDNA from platelets, which are classified as terminally differentiated, anucleate blood cells containing fully functional mitochondria. In addition to being easily accessible, platelets have numerous similarities with neurons and have been frequently utilized as neuronal models. Platelets and neurons both contain mitochondria with the enzyme monoamine oxidase; receptors and transport mechanisms for the uptake and storage of serotonin; as well as APP and the secretases necessary to produce all APP metabolites including amyloid β (Aβ). In fact, platelet APP is synthesized by the megakaryocyte platelet precursor in the bone marrow and may account for 90% of the circulating APP. Platelets show concentrations of APP isoforms equivalent to those found in brain and it has been suggested that platelet APP contributes to the accumulation of Aβ in the brain and its vasculature through the blood brain barrier.

Understanding the origin of acquired mtDNA mutations and causes of expansion have far-reaching implications for understanding human aging and disease risk. These early alterations to mitochondria, which can induce multiple cellular and physiological abnormalities, may represent a shared neurodegenerative mechanism operating across multiple pathologies and present more desirable therapeutic targets than the reversal of the individual pathologies that occur later in the neurodegenerative process. Strategies for selecting against heteroplasmic mtDNA may have therapeutic potential for the treatment of mitochondrial disorders and age-related diseases. For example, rapamycin-induced upregulation of mitophagy results in the progressive decrease in levels of the m.11778G>A (LHON) mutation and partial restoration of cellular ATP levels independent of cell death and mtDNA depletion. By contrast, treatments that enhance mtDNA replication, such as vigorous exercise, should be approached with caution as they could amplify the expansion of deleterious mutations with potentially detrimental long-term consequences. This is exemplified by nucleoside analog anti-retroviral drugs (NRTIs), which have been shown to lead to the progressive accumulation of somatic mtDNA mutations in HIV-infected individuals, mirroring increases in heteroplasmy seen in normal aging. NRTIs, which are powerful inhibitors of mtDNA polymerase, appear to act through the multiplication of preexisting mutations rather than by inducing new ones.

Of the seven complex I mtDNA mutations examined in this disclosure for association with cognitive function increased platelet heteroplasmy at m.10158T>C, p.S34P, ND3 was associated with a clinically significant >3-point decline on the 3MS (highest vs. lowest tertiles). Measuring acquired mtDNA mutations in platelets (where it is clear that platelet APP processing in AD is altered) may reveal novel mechanisms related to early neurodegeneration. In addition, the disclosure analyzed additional mtDNA mutations: 3 for vision, 2 for myopathy and 2 for auditory, all of which show significate association as presented in the Figures. Thus, this study had a number of strengths including the use of a validated, chip-based mtDNA sequencing method, platelet mtDNA, and a well-characterized population-based longitudinal cohort with multiple 3MS assessments. While small sample size and lack of a replication study are acknowledged as limitations, this is a unique dataset that provided a novel opportunity to assess mtDNA heteroplasmy as an early indicator of cognitive decline. If validated, circulating mtDNA heteroplasmy may represent a useful peripheral bio-marker for identifying those at risk of developing cognitive impairment and for monitoring persons who are receiving pharmacologic and behavioral treatments that target the mitochondria.

The present disclosure provides a means to analyze the presence of various mitochondrial nucleic acid sequences in cells from a tissue sample, such as peripheral blood or biopsy. The analysis of various sequences may thus be considered as having been frozen in time. Accordingly, a dynamic scene of mitochondrial gene mutational status is thus captured as static molecules which represent the mutational levels of various gene sequences in time. The disclosure provides a means of correlating the mutational status by direct sequencing of the mtDNA or by generating a plurality of cDNA molecules from the mtRNA population of mitochondria found within a cell. The cDNA molecules may be used to transcribe RNA molecules containing the target sequences of the template RNA containing the target mutation or to transcribe RNA molecules complementary to such sequences. These transcribed molecules may be optionally labeled and used for hybridization to complementary sequences, such as those present on a microarray, to detect and optionally quantify, the mtDNA mutations of various sequences in the mitochondria from which the template RNA was isolated. Alternatively, the transcribed molecules are used to produce labeled cDNA molecules for hybridization to an array.

In another aspect, the technology described herein is utilized in combination with samples of tissue from subjects, preferably human, afflicted with, or suspected of having, a disease or other unwanted condition, such as dementia or Alzheimers Disease (AD). Samples from subjects having the same disease or unwanted condition may be used in combination to identify the mtDNA mutations of gene sequence(s) as correlated with one or more aspects of the disease, or treatment or outcome thereof. Such samples have been collected over time and are often associated with detailed information on the disease, condition, treatment and/or outcomes of the subjects after the sample was taken. Non-limiting examples of such information includes that relating to the diagnosis, prognosis, treatment, response to treatment, and/or actual outcome(s) experienced by the subject over time after collection of the sample. In an alternative aspect, the mutational status of targeted gene sequence(s) may be correlated with the condition of the subject prior to tissue sampling. Non-limiting examples include pre-existing diseases or unwanted conditions, age of disease onset, infection by infectious agents, exposure to mutagens or toxic agents, or genetic disorders. Such correlations are retrospective in nature, as opposed to correlations with outcomes that are to occur, which are prospective in nature. Furthermore, the mutational status of targeted gene sequence(s) may be correlated with information on a disease, condition, treatment and/or outcome of the subject after the sample used to determine gene status is obtained. The technology described herein may thus be used to correlate mitochondrial DNA mutational status with retrospective as well as prospective information from a subject from whom the sample was obtained. The correlations may be used to generate a model to assist clinical diagnostics by application of the correlations between mutation status and outcome(s).

In a further aspect, the disclosure provides for the compilation of the information concerning the mutational status of a plurality of nucleic acid sequences in the mitochondria of a sample into a data structure. The data structure is optionally embedded in a solid medium or other article of manufacture, such as, but not limited to, a computer readable or other electronically readable medium. The arrangement of the data structure permits the ready utilization of the information concerning mtDNA mutational status to be used in methods of interpreting and utilizing such information in combination with an aspect of a disease, or treatment or outcome thereof. Correlations of mutational with an aspect of a disease, or treatment or outcome thereof, may be stored as part of the same data structure or as a separate data structure.

The disclosure also provides for the ability to apply these correlations to the mtDNA mutational status from a sample from another subject to identify the sample has having the same mutational status and the subject as likely to have the same aspect(s) of a disease, or susceptible to the same treatment or outcome thereof. Such samples from another subject include those that are fixed (e.g., FFPE) or not fixed (e.g., peripheral blood sample). The mutational status information from such other samples need not be obtained by the practice of the present disclosure, but rather may be by the use of other means, including, but not limited to, RT-PCR amplification of individual gene sequences and detecting expression of protein(s) encoding by the expressed sequence(s). Such methods of interpreting and utilization are optionally computer implemented.

The nucleic acid mutational status information in such a data structure can include information from one or more tissue samples from six months to over 100 years ago and can include information concerning the post-acquisition treatments and/or outcomes of the subject from which the sample was taken. The information from a plurality of samples from a plurality of subjects may be correlated to identify specific mutational events of one or more mtDNA gene sequences as relevant to an aspect of a disease or the post-acquisition treatments and/or outcomes of the subjects. This information may be applied in whole or in part to form all or part of a clinical definition or identification of a disease or unwanted condition in a subject. It can also be used to prognosticate as to the likely outcome experienced by other subjects with the same mutational profiles in their tissue samples. The information may also be applied to use the mutational status of one or more sequences as defining a population or subpopulation of a larger group based upon diagnosis, prognosis, treatment, response to treatment, and/ or actual outcome(s) correlated with the mutational event(s).

In yet another aspect of the disclosure, methods of applying or interrogating this information to identify a mitochondria-containing sample from another subject as having the same mutational level(s), and thus belonging to a population or subpopulation, are provided. These methods may be optionally computer implemented to maximize the beneficial application of the information that correlates mitochondrial mutational event(s) to diagnosis, prognosis, treatment, response to treatment, and/or actual outcome(s). These methods would be advantageous in clinical applications of the disclosure to assist doctors and other medical personnel with the treatment and/or counseling of patients.

The present disclosure provides for profiling of the mitochondrial mutational status from (routine) clinical biopsies or blood draws. In one embodiment, the disclosure optionally utilizes mitochondria isolated from cells to permit mtDNA mutation profiling. The isolated cells may have a normal or non-normal morphology. Normal cells may also be isolated and used as control cells. The identified mutational op "heteroplasmic" profile may then be optionally used to identify gene sequences, the expression of which define a molecular expression signature for the mitochondria and the condition which they are in. Such conditions include, but are not limited to, disease conditions, types, states, stages, and/or substages or subtypes. In some embodiments, the mutational status signature(s) are used with historical data concerning the subjects from which the tissue samples were obtained to identify the cell(s), and thus a subject containing such cell(s), as eligible or in need of various treatment protocols. This information may then be used to direct treatment (to utilize the more effective treatment) in another subject, or a human patient, identified as having mitochondria (s) with the same signature(s).

The disclosure may be practiced with samples obtained from a blood draw or from samples fixed and embedded with a variety of methods known in the art. Briefly, such methods usually begin with cell containing tissue obtained from a patient afflicted with, or suspected of having, a disease or other unwanted condition. Non-limiting examples of tissue samples include a core biopsy, a removed tumor tissue, and a cytology sample. Other non-limiting examples include fine needle aspirates (FNA), needle biopsies, and ductal lavage samples. Non-limiting examples of tissue type include pancreas, large intestine, muscle, urinary bladder, kidney, lung, brain, lymphoma, and any other tissue of a multicellular organism.

The age of the samples can be from about 6 months to about 100 years old for the practice of the disclosure to correlate mitochondrial heteroplasmy with actual outcomes of the patient from which the samples were taken. Obviously, samples less than about 6 months of age may also be used in the practice of the disclosure, but it may not be possible to correlate mitochondrial mutational status or profile in such samples with actual outcomes of the patient from which they were obtained due to the short time interval. The mutational status of samples without associated outcome information may nonetheless be used in comparison to the mutational status and correlated outcomes generated by the use of the disclosure with older samples. Preferred older samples for correlation of mutational status to actual outcomes are about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 25 years, about 30 years, about 40 years, about 50 years, about 60 years, about 70 years, about 75 years, about 80 years, about 90 years, or about 100 years old.

Information on the mutational profile of various mtDNA sequences may be stored via an appropriate means as preferred by the skilled person. In some embodiments of the disclosure, the information is stored magnetically or electronically, in any form that is computer readable. The data may be stored as raw data or as processed data (such as, but not limited to, normalized, corrected, or in the form of ratios) or as combinations thereof. The processed data can be in the form of raw data that has been converted into a mutational profile index for each mitochondrial gene sequence from a sample. In other embodiments, the information is stored as a data set and/or a data structure. One non-limiting example is storage as a table with stored records. A tabular storage means may be viewed as data fields which store information like a subject identifier (with or without information on mutational status of various sequences from a subject's sample) and/or a gene sequence identifier. These identifiers may also serve as descriptive names for the respective fields. Both the subject identifier and the gene sequence identifier fields can be designated as primary "keys" used to uniquely identify a record. A tabular information storage means of the disclosure can be specific for a disease or unwanted condition and may be stored on a computer-readable medium. They may also be a data structure to support specific manipulation, "look up", or application functions as provided by the instant disclosure.

In another embodiment of the disclosure, the mutational status information is combined with other information about the donor from whom the sample was obtained. Such additional information can include "risk factors" such as higher urinary KIM levels, high levels of serum Aβ42, lower than average scores on cognitive function tests, or any other genotypic or phenotypic characteristic of a human subject that can correlate with, or be indicative of, a mitochondrial-associated disease or disorder. The present disclosure contains numerous examples of such risk factors. Accordingly, "other information" includes risk factors that may be correlated with specific mutations events identified in a mitochondrial nucleic acid sequence.

As used herein, a "mitochondrial-associated" disease or disorder includes any condition, or predisposition to a condition, that results, directly or indirectly, from a mutational event in a mitochondrial genome and falls within clinical parameters indicative of, or a predisposition for, a disorder or disease. Such diseases or disorders include, but are not limited to, Alzheimer's Disease (AD), neurodegenerative disorders such as Parkinson's disease (PD); auto-immune diseases; diabetes mellitus, including Type I and Type II; MELAS, MERFF, arthritis, NARP (Neuropathy; Ataxia; Retinitis Pigmentosa); MNGIE (Myopathy and external ophthalmoplegia; Neuropathy; Gastro-Intestinal; Encephalopathy), LHON (Leber's; Hereditary; Optic; Neuropathy), Kearns-Sayre disease; Pearson's Syndrome; PEO (Progressive External Ophthalmoplegia); congenital muscular dystrophy with mitochondrial structural abnormalities; Wolfram syndrome (DIDMOAD; Diabetes Insipidus, Diabetes Mellitus, Optic Atrophy, Deafness), Leigh's Syndrome, fatal infantile myopathy with severe mtDNA depletion, benign "later-onset" myopathy with moderate reduction in mtDNA; dystonia; schizophrenia; mitochondrial encephalopathy, lactic acidosis, and stroke (MELAS); mitochondrial diabetes and deafness (MIDD); myoclonic epilepsy ragged red fiber syndrome (MERFF); and hyperproliferative disorders, such as cancer, tumors and psoriasis.

In general the subject is a human patient, and such other information includes, but is not limited to, that which is normally obtained in relation to medical or clinical treatment. Non-limiting examples include age, weight, height, medical history as well as health status and/or symptoms or disease type or status at the time the sample was obtained. A further example is information obtained from a pathologist's review of the sample. The latter items are of relevance with respect to patients that are afflicted with, or suspected of being afflicted with, a disease or other unwanted condition. This additional information may also be stored using a tabular storage means as described above or in a separate storage means.

When available, the other information may also include information concerning the patient's diagnosis and care following the isolation of the sample. Generally, such information is that which is normally maintained in a patient's medical history over time to record treatments and outcomes (including further development, eradication, or remissions of a disease) as well as a medical practitioner's notes and/or observations. Non-limiting examples of the latter include cases of unusual genetic makeup of the patient, difficulties in determining a clear diagnosis or course of treatment, and/or unusual disease progression in spite of treatment. Other non-limiting examples of such additional information include that relating to the diagnosis and/or prognosis of the patient, the treatment(s) applied, the responsiveness of the patient and disease to the treatment(s), the presence or absence of side effects from the treatment(s), the cause and age of death of the subject, and other outcome(s) for the patient and disease. In some embodiments of the disclosure, information regarding the treatment(s) applied and the outcome(s) is combined with information concerning mtDNA mutational status.

Additional information relating to outcomes is that which is collected over time, including, but not limited to, information concerning the further progression, eradication, or remission of the disease, the success or failure of the treatment(s), and life span of the patient following treatment. This additional information may also be stored using a tabular storage means as described above or in a separate storage means. Alternatively, it may be combined with a tabular storage means as described above by introduction into a receiver object that is used in combination with the tabular storage means. This combination can be stored in the same medium.

Other information that may be correlated with the mutational status of targeted mitochondrial gene sequence(s) include that of the subject at the time of tissue sampling. Non-limiting examples include pre-existing diseases such as autoimmune disease, unwanted conditions such as excess inflammation, and infection by a bacterial, viral, or fungal agent. Additionally, the same type of information collected about the subject after isolation of the sample may be correlated. Such data is prospective in nature, and includes that from a clinical trial as a non-limiting example. The disclosure may thus be practiced with the use of data that is retrospective and prospective relative to the time of sample isolation. Additionally, the disclosure may be practiced with data that is retrospective and prospective relative to the time of nucleic acid extraction.

The ability to determine and correlate the mutational status of various gene sequences in a sample provides a unique means to relate the status to information concerning disease or patient outcome(s) over time because the sample can serve as a point in time reference from which to correlate the outcome(s). Samples that are sufficiently old to be combined with data concerning disease or patient outcome(s) over time, are thus an archive which can be tapped to correlate mutational events with disease progression and outcome.

Generally, means for the compilation of data are known in the art, but the disclosure provides means for the combination of the mtDNA mutational profile data from samples with additional information concerning a subject or patient as described herein. The means and resulting combinations provided by the instant disclosure provide in part the ability to generate molecular models for disease as well as predictive models to assist in diagnosis and treatment of disease. The generation and use of this combined data are described further below.

Methods of applying or interrogating the "profile" (e.g., mitochondrial profile) or "status" of mtDNA mutation(s) correlated with an outcome include the diagnosis of a subject suspected of having a disease in whole or in part by comparison of the mtDNA mutations in a sample obtained from the subject to one or more profiles generated by the present disclosure. The same or similar profiles indicate the presence of the same disease. The profile may thus be viewed as part of a definition of a disease or as a tool for differential diagnosis to exclude other diseases or unwanted conditions from the diagnosis. The profile may also be considered as defining one or more characteristics of a subject with the same or similar mitochondrial mutational profile. These characteristics include the various outcomes as described herein as well as characteristics that have yet to be recognized. As indicated throughout this disclosure, a mtDNA profile can be combined with other information related to a patients phenotype or genotype. In some cases, mtDNA heteroplasmy information is correlated with additional data derived from a patient or multiple patients. The following non-limiting examples generated by Applicant's support the use of a profile with such information.

Cognitive function: The mitochondrial DNA (mtDNA) m.15244A>G, p.G166G, CytB variant was shown to be associated with a significant decline in cognitive function when combined with data from the Digit Symbol Substitution Test ($\beta=-0.58$, 95% confidence interval (CI) $-0.89$, $-0.28$, p=0.00019). Further, the mtDNA m.14178T>C, p.I166V, ND6 variant was shown to be associated with a significant decline in cognitive function as measured by The Modified Mini-Mental State Examination ($\beta=-0.87$, 95% CI $-1.31$, $-3.86$, p=0.00012).

Amyloid beta (Aβ): The mtDNA m.5046G>A, p.V193I, ND2 variant was shown to be associated with significantly higher serum Aβ42 levels (p=0.0012). Carriers of the m.5046A allele have an elevated mean (SE) Aβ42 of 43.0 (3.5) pg/mL when compared with a mean (SE) Aβ42 of 31.2 (0.59) pg/mL for carriers of the m.5046G allele.

Peripheral nerve function: The mtDNA m.1703C>T variant was shown to be associated with significantly higher nerve conduction velocity (p=0.004). Carriers of the m.1703T allele have an elevated mean (SE) nerve conduction velocity of 53.9 (6.9) m/s when compared with a mean of 42.3 (0.88) m/s for carriers of the m.1703C allele. Further, the mtDNA m.2850C>T variant was shown to be associated with significantly higher nerve conduction velocity (p<0.001). Carriers of the m.2850C allele have an elevated mean (SE) nerve conduction velocity of 48.9 (4.9) m/s when compared with a mean of 42.4 (0.90) m/s for carriers of the m.2850T allele. In addition, the mtDNA m.2639C>T variant was shown to be associated with significantly higher nerve conduction velocity (p=0.004). Carriers of the m.2639T allele have an elevated mean (SE) nerve conduction velocity of 53.9 (6.9) m/s when compared with a mean of 42.3 (0.88) m/s for carriers of the m.2639C allele.

Kidney function: The mtDNA m.3915G>A, ND1 SNP was shown to be associated with significantly higher urinary KIM-1levels (p=1.2e-8). Carriers of the m.3915A allele have elevated mean (SE) KIM-1levels of 2599 (233) pg/ml when compared with a mean of 1207 (38) pg/ml for carriers of the m.3915G allele. Further, the mtDNA m.10589G>A, ND4L SNP was shown to be associated with significantly lower urinary eGFR levels (p=0.0001). Carriers of the m.10589A allele displayed reduced mean (SE) eGFR levels of 57.3 (5.2) ml/minute/1.73 m2 when compared with a mean of 70.8 (0.44) ml/minute/1.73 m2 for carriers of the m.10589G allele. In addition, the mtDNA m.10589G>A, ND4L SNP was shown to be associated with significantly higher urinary KIM-1levels (p=0.0001). Carriers of the m.10589A allele have elevated mean (SE) KIM-1levels of 3000 (444) pg/ml when compared with a mean of 1232 (38) pg/ml for carriers of the m.10589G allele. Moreover, the mtDNA m.15758A>G, CYTB SNP was shown to be associated with significantly higher urinary KIM-1levels (p=0.0001). Carriers of the m.15758A>G allele have elevated mean (SE) KIM-1levels of 3476 (513) pg/ml when compared with a mean of 1074 (46) pg/ml for carriers of the m.15758A allele. Finally, the mtDNA m.6776T>C, COI SNP was shown to be associated with significantly higher urinary albumin/creatinine ratio (p=8.0e-5). Carriers of the m.6776C allele have elevated mean urinary albumin/creatinine ratios 98.1 (16.5) when compared with a mean of 28.9 (3.9) for carriers of the m.6776T allele.

Septic mortality: The mtDNA m.3918G>A SNP was shown to be associated with significantly higher risk of mortality from sepsis (p=0.05). Carriers of the m.3918A allele have elevated risk of septic mortality (Hazard Ratio (HR)=2.2; 95% CI=1.0-4.6) when compared with carriers of the m.3918G allele. Further, the mtDNA m.6152T>C SNP was shown to be associated with significantly higher risk of mortality from sepsis (p=0.05). Carriers of the m.6152C allele have elevated risk of septic mortality (HR=4.3; 95% CI=1.0-19.2) when compared with carriers of the m.6152T allele. In addition, the mtDNA m.11899T>C SNP was shown to be associated with significantly higher risk of mortality from sepsis (p=0.05). Carriers of the m.11899C allele have elevated risk of septic mortality (HR=4.7; 95% CI=1.5-14.9) when compared with carriers of the m.11899T allele. Finally, the mtDNA m.15244A>G SNP was shown to be associated with significantly higher risk of mortality from sepsis (p=0.05). Carriers of the m.15244G allele have elevated risk of septic mortality (HR=2.1; 95% CI=1.0-4.7) when compared with carriers of the m.15244A allele.

The profile may also be used in methods of determining treatment for a subject by using the diagnosis obtained as described above to determine treatment. Alternatively, the profile may include an indication of an efficacious treatment based upon the treatment outcomes of subjects whose samples were used to generate the profile. The same or similar profile of mtDNA mutation(s) in a sample from a subject seeking or in need of treatment would indicate use of the treatment found to be efficacious for the subjects whose samples were used to generate the profile.

Profiles of the disclosure may also be used to provide information concerning prognosis or counseling to a subject afflicted with a disease. Information on disease outcomes that have been associated with mtDNA mutation(s) of the disclosure may be provided to subjects whose tissue samples have been found to have the same or similar gene heteroplasmic profile(s).

Data of the mtDNA mutation status data from a sample obtained by the practice of the methods of the present disclosure, optionally correlated with additional genotypic or phenotypic as described above and throughout the specification, can be organized into one or more data fields of a computer readable medium comprising a plurality of data fields. The data can be in the form of mtDNA mutational values (e.g., heteroplasmic profiles) or indices that may be correlated with other data from the sample donor. The data fields may be optionally organized as one or more datasets and/or one or more data structures. A data field is stored in a range of addresses in the computer readable medium and may be treated as representing mtDNA mutational status data from a sample.

A computer readable medium comprising the data may optionally further comprise an "outcome data" object which serves as a central unit of information that contains not only the subject-specific heteroplasmic profile, but also receives outcome data of the subject(s) from which the sample, and thus mtDNA mutational status, was obtained. The outcome data may also be considered the phenotypic data from the sample donor, which includes donor age, demographics, and history; disease history; diagnosis history; treatments applied and responsiveness thereto; mortality; recurrence of disease, including changes in the form of the disease upon recurrence; and other information as described above. The outcome data object may be stored in a range of addresses separate from the mutational status or in a range of addresses that also stores a data field representing mutational status. When the outcome data object is created, it has locations set aside to store phenotypic information of the outcome(s) experienced by the subject(s). This is a different approach from databases that only store outcome information because the outcome object also contains the mtDNA mutation data. This provides an advantage not previously available because the outcome object can be used to correlate the data with the phenotypic data/outcome(s) to identify the presence of particular mtDNA mutations as linked with one or more phenotypic outcome(s). It also permits the object to be passed from one location or source to another while containing all information relating to one or more outcomes. These benefits permits greater ease and speed of use while minimizing the likelihood of lost information.

In an alternative embodiment of the disclosure, the profile data may be adapted into a spreadsheet program for reviewing the profile data and optionally for comparison and analysis with data from a test sample. The program can be adapted to be capable of analyzing the data in comparison to the profile data to determine the outcome associated with the data. Other analysis modules (software) may be used or developed to utilize the adapted profile data to associate an outcome with a test sample.

The disclosure therefore provides a computer readable medium having a plurality of data fields stored on the medium and representing a data structure, such as mtDNA sequence data and/or patient phenotypic and genotypic profile data, comprising a first data field representing mtDNA mutational data that is to be correlated or analyzed with input (patient phenotypic or genotypic data) information, the first data field being stored in a range of addresses in the computer readable medium; one or more receiver objects that will receive the input information, each receiver object being stored in a separate range of addresses in the computer readable medium, wherein each receiver object comprises a data field adapted for storing input information for correlation or analysis with the first data field.

The present disclosure also provides a system and method for generating mtDNA mutation data for inclusion in a computer readable medium that optionally comprises a receiver object to receive outcome information for correlation with the data. The disclosure further provides a system and method for correlating the data with the outcome information such that mtDNA mutation(s) of one or more mitochondrial gene sequences is/are associated or linked with the outcome. Moreover, the disclosure provides a system and method for generating a mtDNA mutational profile that is correlated with an outcome for inclusion in a computer readable medium. The medium optionally comprises a receiver object to receive test sample mtDNA sequence data for comparison and analysis with additional patient information such as Modified Mini-Mental State Examination data, kidney function data, amyloid beta serum profile data, and/or peripheral nerve function. A system and method for the comparison and analysis is also provided. The systems and methods of the disclosure can be computer implemented and optionally stored as computer executable instructions on a computer readable medium.

In one embodiment, the analysis module is an adapted spreadsheet program which allows correlation, analysis and/or other comparison of the received information with the data. As a non-limiting example, the data may comprise a plurality of prompts that identify specific information items requested for use with the data. Each prompt may represent a row in a spreadsheet program and each information item received from the user may be placed in a column of the spreadsheet. A row may represent a particular outcome, such as sensitivity of a disease to a particular drug treatment, while the columns represent this outcome information for each sample used to generate the mtDNA sequence data to be used. The analysis module in this case would be adapted to correlate the outcome information with the mutational events in the mitochondrial genome to construct a model as described herein.

Because the information received by the receiver object(s) must be communicated to the object(s), some embodiments of the disclosure comprise means for the communication of the information by electronic means. This may be conducted by a communications processor that is optionally directly linked to electronic devices (such as but not limited to databases containing outcome information or a microarray reader/analyzer/image processor) that contain the information to be communicated.

The methods, systems and compositions disclosed herein provide an opportunity for a health care professional to develop a "personalized health plan" for a particular patient. The methods, systems and compositions disclosed herein provide meaningful, actionable information to improve the health or wellness of an individual that is based on the mitochondrial nucleic acid profile of the individual. The health plans provide courses of action that are beneficial to an individual in view of a particular genotype and/or phenotype correlation, and may include administration of therapeutic treatment, monitoring for potential need of treatment or effects of treatment, or making life-style changes in diet, exercise, and other personal habits/activities, which can be personalized based on an individual's mtDNA profile into a personalized health plan. Alternatively, an individual may be given a particular rating that is based on their profile, and in addition, optionally, include other information, such as family history, existing lifestyle habits and geography, such as, but not limited to, work conditions, work environment, personal relationships, home environment, and others. Other factors that may be incorporated include ethnicity, gender, and age. The odds ratio of various dietary and exercise prevention strategies and their association with reducing risks of diseases or conditions can also be incorporated into the rating system.

Furthermore, the personalized health plans may be modified or updated for an individual. Modified or updated personalized health plans may be automatically sent to an individual or their health care manager, for example, if an individual or their health care manager had initially requested automatic updates such as with a subscription plan. Alternatively, the updated personalized health plan may only be sent when requested by an individual or their health care manager. The personalized health plan may be modified or updated based on a number of factors. For example, an individual may have more genetic correlations analyzed and the results used to modify existing recommendations, add additional recommendations, or remove recommendations on the initial personalized health plan. In some embodiments, an individual may have changed certain lifestyle habits/environment, or have more information regarding family history, existing lifestyle habits and geography, such as, but not limited to, work conditions, work environment, personal relationships, home environment, and others, or want to include their updated age to obtain a personalized health plan that incorporates these changes. For example, an individual may have followed their initial personalized health plans, such as reducing cholesterol in their diet or pharmaceutical treatment and thus their personalized health plan recommendations may be modified or their risk or predisposition to heart disease reduced.

The personalized health plan may be reported to an individual, or their health care manager, in a single report with the individual's phenotype profile and/or mtDNA profile. Alternatively, the personalized health plan may be reported separately. The individual can then pursue the recommended actions on their personalized health plan. The individual may choose to consult with their health care manager prior to pursuing any actions on their plan.

The personalized health plan provided can also consolidate a number of condition specific information into a consolidated set of action steps. The personalized health plan can consolidate factors including, but not limited to, the prevalence of each condition, the relative amount of pain associated with each condition, and the type of treatments for each condition. For example, if an individual has an elevated risk of developing dementia (for example, expressed as a Modified Mini-Mental State Examination score), the individual may have a personalized health plan that includes increased consumption of the "treatment" or "therapeutic" as defined in this disclosure.

The personalized health plan recommendations can be of a particular rating, labeling, or categorizing system. Each recommendation may be rated or categorized by a numerical, color, and/or letter scheme or value. The recommendations may be categorized, and further rated. Numerous variations, such as different rating schemes (using letters, numbers or colors; combinations of letters, numbers, and/or colors; different types of recommendations into one or more rating schemes) may be used.

A personalized health plan may be made based on a number of rules, for example, a plurality of rules may be applied to a mtDNA mutational status to determine the association of an individual's status with a specific phenotype. The determinations may also incorporate factors that are specific to an individual, such as ethnicity, gender, lifestyle, age, environment, family medical history, personal medical history, and other known phenotypes. The incorporation of the specific factors may be by modifying existing rules to encompass these factors. Alternatively, separate rules may be generated by these factors and applied to a phenotype determination for an individual after an existing rule has been applied.

A "biomarker" in the context of the disclosure refers to a mutation or degree of heteroplasmy in loci disclosed herein or to a polymorphism, mutation or heteroplasmy which is in linkage disequilibrium (LD) with one or more disclosed biomarkers, or to an organic biomolecule which is related to a biomarker identified at a mtDNA loci and which is differentially present in samples taken from subjects (patients). It will be recognized based upon the data and discussion herein that these disease mutations will interact to affect disease (for example, carrying high levels of heteroplasmy at more than one site can impact the presence or severity of disease or physical decline). This will not be through LD but rather be an epistatic interaction. LD is the appropriate term for inherited SNPs that are physically liked along the chromosome. The heteroplasmic mutations may or may not be affected by this (e.g. heteroplasmic mutations can accumulate independently across the mtDNA). An "organic biomolecule" refers to an organic molecule of biological origin comprising steroids, amino acids, nucleotides, sugars, polypeptides, polynucleotides, complex carbohydrates and lipids. A biomarker is differentially present between two samples if the amount, structure, function or biological activity of the biomarker in one sample differs in a statistically significant way from the amount, structure, function or biological activity of the biomarker in the other sample.

Biomarkers can reflect a variety of disease characteristics, including the level of exposure to an environmental or genetic trigger, an element of the disease process itself, an intermediate stage between exposure and disease onset, or an independent factor associated with the disease state but not causative of pathogenesis. Depending on the specific characteristic, biomarkers can be used to identify the risk of developing an illness (antecedent biomarkers), aid in identifying disease (diagnostic biomarkers), or predict future disease course, including response to therapy (prognostic biomarkers).

A genotype is an unphased 5' to 3' sequence of nucleotide pair(s) found at a set of one or more polymorphic sites in a locus on a pair of homologous chromosomes or mtDNA in an individual. As used herein, genotype includes a full-genotype and/or a sub-genotype.

Genotyping is a process for determining a genotype of an individual.

A "haplotype," as described herein, refers to a combination of genetic markers ("alleles"). A haplotype can comprise two or more alleles and the length of a genome region comprising a haplotype may vary from few hundred bases up to hundreds of kilobases. As it is recognized by those skilled in the art the same haplotype can be described differently by determining the haplotype defining alleles from different nucleic acid strands. The haplotypes described herein are differentially present in individuals with mtDNA mutant-associated diseases and disorders than in individuals without mtDNA mutant-associated diseases and disorders. Therefore, these haplotypes have diagnostic value for risk assessment, diagnosis and prognosis. Detection of haplotypes can be accomplished by methods known in the art used for detecting nucleotides at polymorphic sites. Haplotypes found more frequently have predictive value for predicting susceptibility to a disease or disorder. Moreover, although the presence of a particular haplotype is diagnostic/prognostic, the disclosure demonstrates that the mere presence of a pathogenic/mutant haplotype is not necessarily indicative of disease. Rather the disclosure demonstrates that the "level" of pathogenic mtDNA by measuring heteroplasmy is a better indicator of risk, diagnosis and prognosis. In other words, the disclosure uses, alone or in combination with methods of determining a haplotype, a measure of the heteroplasmy in a subject (i.e., the level of mutant mitochondrial organelles in a subject to the total mitochondrial organelles).

Haplotype pair is two haplotypes found for a locus in a single individual.

Haplotyping is the process for determining one or more haplotypes in an individual and includes use of family pedigrees, molecular techniques and/or statistical inference.

A genetic locus refers to a location on a chromosome or DNA molecule corresponding to a gene or a physical or phenotypic feature, where physical features include polymorphic sites.

A polymorphism refers to the sequence variation observed in an individual at a polymorphic site. Polymorphisms include nucleotide substitutions, insertions, deletions and microsatellites and may, but need not, result in detectable differences in gene expression or protein function. A single nucleotide polymorphism (SNP) is a single change in the nucleotide variation at a polymorphic site. Thus, a nucleotide position in DNA at which more than one sequence is possible in a population, is referred to herein as a "polymorphic site" or "polymorphism". Where a polymorphic site is a single nucleotide in length, the site is referred to as a single-nucleotide polymorphism or SNP. For example, if at a particular chromosomal location, one member of a population has an adenine and another member of the population has a thymine at the same position, then this position is a polymorphic site, and, more specifically, the polymorphic site is a SNP. Polymorphic sites may be several nucleotides in length due to insertions, deletions, conversions or translocations. Each version of the sequence with respect to the polymorphic site is referred to herein as an "allele" of the polymorphic site. Thus, in the previous example, the SNP allows for both an adenine allele and a thymine allele.

Typically, a reference nucleotide sequence is referred to for a particular gene, e.g., in NCBI databases ([www.]ncbi.nlm.nih.gov). Alleles that differ from the reference are referred to as "variant" alleles. The polypeptide encoded by the reference nucleotide sequence is the "reference" polypeptide with a particular reference amino acid sequence, and polypeptides encoded by variant alleles are referred to as "variant" polypeptides with variant amino acid sequences. Nucleotide sequence variants can result in changes affecting properties of a polypeptide. These sequence differences, when compared to a reference nucleotide sequence, include insertions, deletions, conversions and substitutions: e.g. an insertion, a deletion or a conversion may result in a frame shift generating an altered polypeptide; a substitution of at least one nucleotide may result in a premature stop codon, amino acid change or abnormal mRNA splicing; the deletion of several nucleotides, resulting in a deletion of one or more amino acids encoded by the nucleotides; the insertion of several nucleotides, such as by unequal recombination or gene conversion, resulting in an interruption of the coding sequence of a reading frame; duplication of all or a part of a sequence; transposition; or a rearrangement of a nucleotide sequence. Such sequence changes alter the polypeptide and can lead to various diseases and disorders. For example, a nucleotide change resulting in a change in polypeptide sequence can alter the physiological properties of a polypeptide dramatically by resulting in altered activity, distribution and stability or otherwise change the properties of a polypeptide. Alternatively, nucleotide sequence variants can result in changes affecting transcription of a gene or translation of its mRNA. A polymorphic site located in a regulatory region of a gene may result in altered transcription of a gene, e.g., altered transcription rate or altered response to transcription factors. A polymorphic site located in a region corresponding to the mRNA of a gene may result in altered translation of the mRNA, e.g., by inducing stable secondary structures to the mRNA and affecting the stability of the mRNA. Early detection and treatment of patients with variant coding sequences can lower or prevent long term risks and death.

The terms "correlate" or "correlation" or equivalents thereof refer to an association between the mutational status of one or more mtDNA sequences and a physiologic state of a cell, or a patient, to the exclusion of one or more other states by use of the methods as described herein. The disclosure provides for the correlation between changes in mtDNA sequence at specific target sequences to identify "heteroplasmy." The presence or absence, or increase or decrease, in specific mutational events may be readily expressed in the form of a ratio. The term "correlating," as used herein in reference to the use of diagnostic and prognostic indicators, refers to comparing the presence or amount of the indicator in a patient to its presence or amount in persons known to suffer from, or known to be at risk of, a given condition; or in persons known to be free of a given condition. As throughout the disclosure, the mutational status mtDNA in a patient sample can be compared to mutational profiles known to be associated with a disease, such as dementia, AD, sepsis, kidney disease, and condition related to peripheral nerve function. The sample's mutational status can optionally be correlated with other phenotypic and genotypic characteristics of a patient and used to arrive at a diagnosis; that is, the skilled artisan can use the profile (e.g., mtDNA mutational status alone or in combination with other patient information) to determine whether the patient has, or is predisposed to having, a disease, and respond accordingly. Alternatively, the profile can be compared to a profile known to be associated with a good outcome (e.g., the absence of, or non-predisposition for a disease, etc.).

A "mtDNA health panel", as used herein, includes any composition or product that provides for the targeted identification of specific sequences in a mitochondrial genome. Such panels are known to the skilled artisan and include any next generation sequencing panel or PCR-based panel that can detect and identify targeted sequences present in mitochondrial DNA. The progression, susceptibility to, or remission of a disease can be monitored by contacting test samples from an individual taken at different times with the mtDNA health panel targeted for mitochondrial mutations. For example, a second test sample is taken from the patient and contacted with the mtDNA health panel days or weeks after the first test sample. Alternatively, the second or subsequent test samples can be taken from the patient and tested against the mtDNA health panel at regular intervals, such as daily, weekly, monthly, quarterly, semi-annually, or annually. By testing the patient's test samples at different times, the presence of targeted mitochondrial mutations and therefore the stage of, or susceptibility to, the disease can be compared. A further embodiment of the disclosure is a method of monitoring one or more target mitochondrial mutations in test samples from an individual diagnosed as having, or susceptible to, a disease associated with mitochondrial dysfunction comprising: a) contacting a first test sample from the individual with one or more target mtDNA health panels; b) detecting one or more targeted mitochondrial mutations in the first test sample; c) contacting a second test sample from the individual with a target mtDNA health panel; d) detecting the presence of the one or more target mtDNA mutations in the second test sample; and e) comparing the presence of the one or more targeted mitochondrial mutations against the one or more target mtDNA mutations from the first test sample with the one or more targeted mitochondrial mutations from the second test sample, correlating the results to determine the difference in mutation profile, and determining the presence or absence of heteroplasmy of the targeted sequences.

The progression of the disease is further monitored by quantitatively comparing the amounts of targeted mitochondrial mutations detected by a mtDNA health panel comprising any of the mutational events described herein, including those described in Table II. Accordingly, another embodiment of the disclosure further comprises detecting the presence of the one or more targeted mitochondrial mutations against the one or more mtDNA health panels in the first test sample and the second test sample; and comparing the amount of the one or more targeted mitochondrial mutations from the first test sample with the amount of the one or more targeted mitochondrial mutations from the second test sample.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein.

"Detection" or "detect" includes any means of detecting, including direct and indirect detection of mtDNA sequences changes therein.

"Disease" refers to a change in the normal status of a living organism or a tissue or organ thereof that impairs the performance of the organism's physiological functions. A disease may be a result of exposure to environmental factors (such as, but not limited to, chemical agents or radiation), to an infective agent (such as, but not limited to, bacteria, viruses, or parasites), to congenital defects of the organism (such as, but not limited to, genetic mutations which may manifest in combination with environmental factors or at different times in the life of the organism). A disease may also be due to a combination of the above as well as descriptive of a set of related diseases. A non-limiting example of the latter is the use of the term "breast cancer" to refer to a group of cancer diseases in breast tissue as well as a group of subtypes of breast cancer.

As used herein, "treatment" or "therapeutic" includes any compound, drug, composition or supplement known to prevent mtDNA mutations and/or increase mitochondrial function. Exemplary therapeutics and dosage regimens include, but are not limited to: CoQ10 (5-15 mg/kg/day), Levo-carnitine (Carnitor) (30 mg/kg/day, typical maximum of 100 mg/kg/day), Riboflavin (B2) (100-400 mg a day), Acetyl-L-Carnitine (250-1000 mg per day), Thiamine (B1) (50-100 mg a day, Niacin (B3) (50-100 mg a day), Vitamin E (200-400 IU; 1-3 times a day), Vitamin C (100-500 mg; 1-3 times a day), Lipoic Acid (a-lipoate) (60-200 mg; 3 times a day), Selenium (25-50 micrograms a day), β-carotene (10,000 IU; every other day to daily), Biotin (2.5-10 mg a day), Folic Acid (1-10 mg a day), Calcium (variable), Magnesium (variable), Phosphorus (variable), Succinate (6 gm per day), Creatine (5 gm bid after initial load (adults), Uridine (variable), Citrates (variable), Prednisone (variable), Vitamin K3 (5-30 mg per day).

A "prognosis" is often determined by examining one or more "prognostic indicators", the presence or amount of which in a patient (or a sample obtained from the patient) signal a probability that a given course or outcome will occur. For example, when one or more prognostic indicators reach a sufficiently high level (e.g., heteroplasmy at one or more nucleotide sequences in a mitochondrial genome) in samples obtained from such patients, the level may signal that the patient is at an increased probability of having a disease or condition in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient.

The phrase "determining the prognosis" as used herein refers to methods by which the skilled artisan can predict the course or outcome of a condition in a patient. The term "prognosis" does not refer to the ability to predict the course or outcome of a condition with 100% accuracy, or even that a given course or outcome is more likely to occur than not. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. For example, in individuals not exhibiting the condition, the chance of a given outcome may be about 3%. In some embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to +/−1%. Accordingly, "prognosis" includes determining whether a patient is predisposed to a particular condition or disease, even if the patient does not manifest symptoms of the condition or disease.

Although certain terms (as further described above and below) are used interchangeably between genomic DNA and mtDNA, the concept that mutations in DNA, whether genomic or mtDNA, cause disease or disorders is recognized. For example, codon usage for mtDNA differs slightly from the universal code. For example, UGA codes for tryptophan instead of termination, AUA codes for methionine instead of isoleucine, and AGA and AGG are terminators instead of coding for arginine.

The disclosure describes novel diagnostic biomarkers in mtDNA for various mtDNA-associated disease and disorders including, for example, atherosclerosis and related cardiovascular diseases such as coronary heart disease (CHD), cerebrovascular disease, intermittent claudication, congestive heart failure and other manifestations of arteriosclerosis, hypertension, obesity and type 2 diabetes. The disclosure provides (i) novel genes, loci and individual biomarkers associated with these conditions as well as (ii) predictive measurements based upon the amount, weight or load of mutations in a subject's mtDNA. As mentioned above, heteroplasmy is the combination of both normal and mutant mitochondria and mitochondrial DNA. The "weight" or "load" of one form (e.g., a mutant form) of the set of heteroplasmic markers in a subject's cells is demonstrated herein to be associated with an increased risk. In other words, if a subject has both a normal and mutant mitochondria, the mere fact that a small number mitochondria carrying mutated DNA is not necessarily indicative of a disease, disorder or risk thereof. Rather, the disclosure demonstrates that the "level" or "load" of mitochondria having mutant DNA of a particular form is important for determining a disease, disorder or risk thereof. The disclosure further relates to physiological and biochemical routes and pathways related to these genes, as well as gene and other therapies modifying the genes or their products.

For example, in one embodiment, the disclosure provides methods of determining the risk, diagnosis or prognosis of a mitochondrial-associated disease or disorder, by measuring the amount of mutant mitochondria compared to the total amount mitochondria in the subject, wherein when the level of mutant mitochondria is above a threshold for a particular disease associated with a define mutant locus, then the subject is at risk, can be diagnosed or a prognosis identified based upon the level. For example, the disclosure provides a method of determining a risk of a clinically relevant cognitive decline comprising, (a) isolating mitochondria or mtDNA; (b) measuring a heteroplasmy at 10158 of the mtDNA; (c) determining the frequency of 10158T compared to 10158C; wherein when the frequency of 10158C is greater than 10% of the total number of alleles (i.e., 10158C+10158T) then the subject is at risk for clinically significant cognitive decline as measured by the Modified Mini-Mental State Examination. In another embodiment, a method of determining a risk of a clinically relevant vision loss is provided, comprising: (a) isolating mitochondria or mtDNA; (b) measuring a heteroplasmy at 11778 of the mtDNA; (c) determining the frequency of 11778A compared to 11778G; wherein when the frequency of 11778A is greater than 9.5% of the total number of alleles (11778A+11778G) then the subject is at risk for clinically significant vision loss as measured by contrast sensitivity testing. In yet another embodiment, the disclosure provides a method of determining a risk of a clinically relevant mobility decline comprising: (a) isolating mitochondria or mtDNA; (b) measuring a heteroplasmy at 5703 of the mtDNA; (c) determining the frequency of 5703A compared to 5703G; wherein when the frequency of 5703A is greater than 11% of the total number of alleles (5703A+5703G) then the subject is at risk for clinically significant mobility decline as measured by 400 m walking speed. In yet another embodiment, the disclosure provides a method of determining a risk of a clinically relevant hearing loss comprising: (a) isolating mitochondria or mtDNA; (b) measuring a heteroplasmy at 7445 of the mtDNA; (c) determining the frequency of 7445A compared to 7445G; wherein when the frequency of 7445A is greater than 25% of the total number of alleles (7445A+7445G) then the subject is at risk for clinically significant high frequency hearing loss as measured by high frequency hearing testing. In one embodiment, the DNA source for analysis can be from any suitable sample, including whole blood or white blood cells. Since whole blood and white blood cells are much more common in the clinical setting these provide sufficient sources for measuring mtDNA. In various embodiments of any of the foregoing, the mitochondria or mtDNA can be isolated from a postmitotic cell population. For example, the mitochondria or mtDNA can be isolated platelet cells. The mtDNA can be measured using various methods known in the art including oligo-ligation assays, microarrays such as nucleic acid arrays, sequencing methods and the like. In various embodiments, the mtDNA is isolated and can be detectably labeled with a non-natural fluorescent tag or radioactive label. In yet another embodiment, the mtDNA is measured by digital methods (e.g., a CCD or other optical device obtains a signal from a sample and can convert that signal to a value associated with the level of heteroplasmy).

Various techniques, as discussed more fully herein below, are available for detecting the specific mutations in mitochondrial genes, including those associated with complex I nucleic acid sequences. The analyses of the isolated nucleic acids can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof.

The detection methods include, for example, cloning and sequencing, ligation of oligonucleotides, use of the polymerase chain reaction and variations thereof, use of single nucleotide primer-guided extension assays, hybridization techniques using target-specific oligonucleotides, next generation sequencing techniques, and sandwich hybridization methods.

Mutational analysis can also be carried out by methods based on ligation of oligonucleotide sequences which anneal immediately adjacent to each other on a target DNA or RNA molecule (Wu and Wallace, Genomics 4: 560-569 (1989); Landren et al., Science 241: 1077-1080 (1988); Nickerson et al., Proc. Natl. Acad. Sci. 87: 8923-8927 (1990); Barany, F., Proc. Natl. Acad. Sci. 88: 189-193 (1991)). Ligase-mediated covalent attachment occurs only when the oligonucleotides are correctly base-paired. The Ligase Chain Reaction (LCR) and the oligonucleotide ligation assay (OLA), which utilize the thermostable Taq ligase for target amplification, are particularly useful for interrogating AD mutation loci. The elevated reaction temperatures permit the ligation reaction to be conducted with high stringency (Barany, F., PCR Methods and Applications 1: 5-16 (1991)) (Grossman, P. D. et al., Nucl. Acids. Res. 22: 4527-4534, (1994)).

Analysis of point mutations in DNA can also be carried out by using the polymerase chain reaction (PCR) and variations thereof. Mismatches can be detected by competitive oligonucleotide priming under hybridization conditions where binding of the perfectly matched primer is favored (Gibbs et al., Nucl. Acids. Res. 17: 2437-2448 (1989)).

Genotyping analysis of the mitochondrial genes can also be carried out using single nucleotide primer-guided extension assays, where the specific incorporation of the correct base is provided by the high fidelity of the DNA polymerase (Syvanen et al., Genomics 8: 684-692 (1990); Kuppuswamy et al., Proc. Natl. Acad. Sci. U.S.A. 88: 1143-1147 (1991)).

Detection of single base mutations in target nucleic acids can be conveniently accomplished by differential hybridization techniques using allele-specific oligonucleotides (Suggs et al., Proc. Natl. Acad. Sci. 78: 6613-6617 (1981); Conner et al., Proc. Natl. Acad. Sci. 80: 278-282 (1983); Saiki et al., Proc. Natl. Acad. Sci. 86: 6230-6234 (1989)). Mutations can be diagnosed on the basis of the higher thermal stability of the perfectly matched probes as compared to the mismatched probes. The hybridization reactions can be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

Another method for analysis of a biological sample for specific mutations in the mitochondrial genes is a multiplexed primer extension method. In this method primer is hybridized to nucleic acid suspected of containing a mutation such that the primer is hybridized 3' to the suspected mutation. The primer is extended in the presence of a mixture of one to three deoxynucleoside triphosphates and one of three chain terminating deoxynucleoside triphosphates selected such that the wild-type extension product, the mutant DNA-derived extension product and the primer each are of different lengths. These steps can be repeated, such as by PCR or RT-PCR, and the resulting primer extended products and primer are then separated on the basis of molecular weight to thereby enable identification of mutant DNA-derived extension product.

A nucleic acid array refers to a plurality of oligonucleotides at addressable (i.e., known positions) on a solid substrate. The oligonucleotide arrays for use in the disclosure can be made by spotting, e.g., applying arrays of probes to a solid substrate, or to the synthesis of probes in place on a solid substrate. A "substrate" can include any solid substrate that can be used to immobilize nucleic acids in an array format such as a glass slide, microplate and the like. As used herein "glass slide" refers to a small piece of glass that can be of the same dimensions as a standard microscope slide. As used herein, "prepared substrate" refers to a substrate that is prepared with a substance capable of serving as an attachment medium for attaching the probes to the substrate, such as poly Lysine. As used herein, "sample" refers to a composition containing human mitochondrial DNA that can be genotyped. As used herein, "quantitative hybridization" refers to hybridization performed under appropriate conditions and using appropriate materials such that the sequence of one nucleotide allele (a single nucleotide polymorphism) can be determined, such as by hybridization of a molecule containing that allele to two or more probes, each containing different alleles at that nucleotide locus, such probes or sample DNA being detectably labeled in order to quantify the amount of DNA that hybridizes using techniques known in the art.

As used herein, an isolated nucleic acid is a nucleic acid outside of the context in which it is found in nature. The term covers, for example: (a) a DNA which has the sequence of part of a naturally-occurring genomic or mtDNA molecule but is not flanked by both of the coding or noncoding sequences that flank that part of the molecule in the genome or mitochondrial DNA of the organism in which it naturally occurs; (b) a nucleic acid incorporated into a vector or into the genomic DNA of a prokaryote or eukaryote in a manner such that the resulting molecule is not identical to any naturally-occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein, or a modified gene having a sequence not found in nature. For example, mtDNA can be isolated and the whole length of the mtDNA can be PCR amplified in 2 separate reactions, which can be subsequently fractionated into smaller 100-200 base pair fragments for sequencing. The term "nucleic acid" as used herein, includes a polymer comprising ribonucleosides and/or deoxyribonucleosides that are covalently bonded, typically by phosphodiester linkages between subunits, but in some cases by phosphorothioates, methylphosphonates, and the like. Nucleic acids further include, but are not limited to, gDNA; circular DNA; low molecular weight DNA, plasmid DNA; circulating DNA; hnRNA; mRNA; noncoding RNA (ncRNA), including but not limited to rRNA, tRNA, miRNA (micro RNA), siRNA (small interfering RNA), snoRNA (small nucleolar RNA), snRNA (small nuclear RNA) and stRNA (small temporal RNA); fragmented or degraded nucleic acids; nucleic acid obtained from subcellular organelles such as mitochondria (mtDNA) or chloroplasts; and nucleic acid obtained from microorganisms, parasites, or DNA or RNA viruses that may be present in a biological sample. Synthetic nucleic acid sequences that may or may not include nucleotide analogs that are added or "spiked" into a biological sample are also within the scope of the invention.

As used herein, "nucleotide locus" refers to a nucleotide position of a mitochondrial genome such as the human mitochondrial genome. As used herein, "loci" refers to more than one locus. As used herein, "nucleotide allele" refers to a single nucleotide at a selected nucleotide locus from a selected sequence when different bases occur naturally at that locus in different individuals. Nucleotide allele information is typically provided as the nucleotide locus number and the base that is at that locus, such as, e.g., 3796C, which means that at human mitochondrial position 3796 in the Cambridge sequence, there is a cytosine (C).

As used herein, "target" or "target sample" refers to the collection of nucleic acids used as a sample for array or sequencing analysis. The target is interrogated by, for example, the probes of an array or through sequencing technology. A "target" or "target sample" may be a mixture of several samples that are combined. For example, an experimental target sample may be combined with a differently labeled control target sample and hybridized to an array, the combined samples being referred to as the "target" interrogated by the probes of the array during that experiment. As used herein, "interrogated" means tested. Probes, targets, and hybridization conditions are chosen such that the probes are capable of interrogating the target, i.e., of hybridizing to complementary sequences in the target sample.

As used herein, "increased likelihood of developing a disease or disorder" refers to a higher than normal probability of having a particular disease or disorder compared to a reference population. The probability can be determined using the level of mutant mitochondria or mtDNA present in a sample compared to the total mitochondria or mtDNA. A value that is 5%, 10%, 20%, 30% or more above a threshold value is indicative of an increased probability. For example, as mentioned above, when the frequency of 10158C is greater than 10% of the total number of alleles (i.e., 10158C+10158T) then the subject is at risk for clinically significant cognitive decline as measured by the Modified Mini-Mental State Examination. If the frequency is 5% higher than the threshold value of 10% (e.g., 15%), then there is an increased probability of significant cognitive decline.

"Probes" or "primers" are oligonucleotides that hybridize in a base-specific manner to a complementary strand of nucleic acid molecules. By "base specific manner" is meant that the two sequences must have a degree of nucleotide complementarity sufficient for the primer or probe to hybridize to its specific target. Accordingly, the primer or probe sequence is not required to be perfectly complementary to the sequence of the template. Non-complementary bases or modified bases can be interspersed into the primer or probe, provided that base substitutions do not inhibit hybridization. The nucleic acid template may also include "nonspecific priming sequences" or "nonspecific sequences" to which the primer or probe has varying degrees of complementarity. Probes and primers may include modified bases such as peptide nucleic acids (Nielsen P E et al, 1991). In another embodiment, the probe or primer may further comprise a detectable label, e.g., radioisotope, fluorescent compound, luminescent compound, enzyme, or enzyme co-factor. Probes and primers to a heteroplasmy marker are available in the art or can easily be designed using the flanking nucleotide sequences based on Revised Cambridge Reference Sequence (rCRS) of the Human Mitochondrial DNA and standard probe and primer design tools.

An oligonucleotide probe or a primer refers to a nucleic acid molecule of between 8 and 2000 nucleotides in length, or is about 6 and 1000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the disclosure under a particular set of conditions may be empirically determined by one of skill in the art.

Oligonucleotide primers and probes can be prepared by any suitable method, including, for example, cloning and restriction of appropriate sequences and direct chemical synthesis. The oligonucleotide primers and probes can contain conventional nucleotides, as well as any of a variety of analogs. For example, the term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-($C_1$-$C_6$)alkoxyribose, 2'-($C_5$-$C_{14}$)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$-$C_6$)alkylribose, 2'-deoxy-3'-($C_1$-$C_6$)alkoxyribose and 2'-deoxy-3'-($C_5$-$C_{14}$)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). Exemplary LNA sugar analogs within a polynucleotide include, but are not limited to, the structures: where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N_9$-position of the nucleotide base. When the nucleotide base is pyrimidine, e.g. C, T or U, the pentose sugar is attached to the $N_1$-position of the nucleotide base, except for pseudouridines, in which the pentose sugar is attached to the $C_5$ position of the uracil nucleotide base (see, e.g., Kornberg and Baker, (1992) DNA Replication, 2nd Ed., Freeman, San Francisco, Calif.). The 3' end of the probe can be functionalized with a capture or detectable label to assist in detection of a target polynucleotide or of a polymorphism.

Any of the oligonucleotides or nucleic acids of the disclosure can be labeled by incorporating a detectable label measurable by spectroscopic, photochemical, biochemical, immunochemical, or chemical means. For example, such labels can comprise radioactive substances (e.g., $^{32}$P, $^{35}$S, $^3$H, $^{125}$I), fluorescent dyes (e.g., 5-bromodesoxyuridin, fluorescein, acetylaminofluorene, digoxigenin), biotin, nanoparticles, and the like. Such oligonucleotides are typically labeled at their 3' and 5' ends.

A probe refers to a molecule which can detectably distinguish changes in a nucleic acid sequence, such as mtDNA mutations, or can distinguish between target molecules differing in structure. Detection can be accomplished in a variety of different ways depending on the type of probe used and the type of target molecule. Thus, for example, detection may be based on discrimination of activity levels of the target molecule, but typically is based on detection of specific binding. Examples of such specific binding include nucleic acid probe hybridization. Thus, for example, probes can include nucleic acid hybridization probes (including primers useful for polynucleotide amplification and/or detection). Thus, in one embodiment, the detection of the presence or absence of the at least one target polynucleotide involves contacting a biological sample with a probe or primer pair, typically an oligonucleotide probe or primer pair, where the probe/primers hybridizes with a form of a target polynucleotide in the biological sample containing a complementary sequence, where the hybridization is carried out under selective hybridization conditions. Such an oligonucleotide probe can include one or more nucleic acid analogs, labels or other substituents or moieties so long as the base-pairing function is retained.

In diagnostic assays determination of the nucleotides present in one or more heteroplasmy markers disclosed herein in an individual's nucleic acid can be done by any method or technique which can accurately determine nucleotides present in a polymorphic site. Numerous suitable methods have been described in the art. These methods include, but are not limited to, hybridization assays, ASO-hybridization assays, restriction fragment length polymorphism assays, SSCP-analysis, ligation assays, primer extension assays, enzymatic cleavage assays, chemical cleavage assays, Sanger sequencing, next gen sequencing, digital PCR and any combination of these assays. The assays may or may not include PCR, real-time PCR, solid phase step, a microarray, modified oligonucleotides, labeled probes or labeled nucleotides, enzyme-linked immunosorbent assays, or sequencing and the assay may be multiplex or singleplex. As it is obvious in the art the nucleotides present in a polymorphic site can be determined from either nucleic acid strand or from both strands.

A reference or control population refers to a group of subjects or individuals who are predicted to be representative of the genetic variation found in the general population having a particular genotype, phenotype, or mitochondrial heteroplasmic profile. Typically, the reference population represents the genetic variation in the population at a certainty level of at least 85%, typically at least 90%, least 95% and but commonly at least 99%. The reference or control population can include subjects who individually have not demonstrated any mitochondrial associated disease or disorder and can include individuals whose family line does not or has not demonstrated any mitochondrial associated diseases or disorder.

As used herein, "physiological condition" includes diseased conditions, healthy conditions, and cosmetic conditions. Diseased conditions associated with mutant mitochondrial DNA include, but are not limited to, metabolic diseases such as diabetes, hypertension, and cardiovascular disease. Healthy conditions include, but are not limited to, traits such as increased longevity. Physiological conditions include cosmetic conditions. Cosmetic conditions include, but are not limited to, traits such as amount of body fat. Physiological conditions can change health status in different contexts, such as for the same organism in a different environment. Such different environments for humans are different cultural environments or different climatic contexts such as are found on different continents.

As used herein, "extended longevity" or "extended lifespan" refers to living longer than the average expected lifespan for the population to which one belongs. As used herein, "centenarian" refers to an extended lifespan that is at least 100 years.

As used herein, "abnormal energy metabolism" in an individual who is non-native to the geographical region in which he lives refers to energy metabolism that differs from that of the population that is native to where the individual lives. As used herein, "abnormal temperature regulation" in such an individual refers to temperature regulation that differs from that of the population that is native to where he lives. As used herein, "abnormal oxidative phosphorylation" in such an individual refers to oxidative phosphorylation that differs from that of the population that is native to where he lives. As used herein, "abnormal electron transport" in such an individual refers to electron transport that differs from that of the population that is native to where he lives. As used herein "metabolic disease" of such an individual refers to metabolism that differs from that of the population that is native to where he lives. As used herein, "energetic imbalance" of such an individual refers to a balance of energy generation or use that differs from that of the population that is native to where he lives. As used herein, "obesity" of such an individual refers to a body weight that, for the height of the individual, is 20% higher than the average body weight that is recommended for the population native to where the individual lives. As used herein, "amount of body fat" of such an individual refers to a low or high percentage of body fat relative to what is recommended for the population that is native to where he lives.

Unless defined otherwise all technical and scientific terms used herein have the same meaning as commonly understood to one of ordinary skill in the art to which this disclosure belongs. The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Primers, oligonucleotides and polynucleotides employed in the present disclosure can be generated using standard techniques known in the art.

The following examples are intended to illustrate but not limit the disclosure. While they are typical of those that might be used, other procedures known to those skilled in the art may alternatively be used.

EXAMPLES

Participants.
138 Health, Aging and Body Composition (Health ABC) participants of European ancestry were used in the study. Health ABC is a prospective cohort study of 3,075 community-dwelling black and white men and women living in Memphis, Tenn., or Pittsburgh, Pa., and aged 70-79 years at recruitment in 1996-1997. Participants were recruited from a random sample of white and black Medicare-eligible people within designated zip code areas. Participants had to report no difficulty with activities of daily living, walking a quarter of a mile, or climbing 10 steps without resting. They were free of life-threatening cancer diagnoses. The sample was 51% women and 41% of participants were black. Participants self-designated race/ethnicity classified as Asian/Pacific Islander, black/African American, white/Caucasian, Latino/Hispanic, and/other. The study was designed to have sufficient numbers of black participants to allow estimates of the relationship of body composition to functional decline. All eligible participants signed a written informed consent, approved by the institutional review boards at the clinical sites. This study was approved by the institutional review boards of the clinical sites and the coordinating center (University of California, San Francisco).

Mitochondrial DNA Sequencing.

Complete mtDNA was extracted from platelets collected at year two using the Gentra PureGene Kit (Qiagen, Hilden, Germany) and sequenced using the Affymetrix Mitochondrial Resequencing Array 2.0 (MitoChip, Affymetrix, Santa Clara, Calif.). The MitoChip interrogates the forward and reverse strands of the 16.5 kb mitochondrial genome for a total of ~30 kb sequence, enables the detection of known and novel mutations and has redundant probe tiling for detecting the major human mitochondrial haplotypes and known disease-related mutations. Built-in redundancy via independent probe sets also allows a test of within-chip reproducibility. Briefly, the entire mitochondrial genome was first amplified in two long-range PCR reactions using LA PCR Kit (Takara Bio U.S.A., Madison, Wis.) for each sample using two sets of overlapping primers. Mitochondrial fragments were amplified and prepared for array hybridization according to the Affymetrix protocol for GeneChip CustomSeq Resequencing Array. The resulting PCR products were assessed qualitatively by 1% agarose gel electrophoresis and purified using a Clonetech Clean-Up plate (Clonetech, Mountain View, Calif.). The purified DNA was quantified by PicoGreen and for selected samples, confirmed by Nano-Drop measurements. The amplicons were pooled at equimolar concentrations. Chemical fragmentation was performed and products were confirmed to be in the size range of 20-200 bp by 20% polyacrylamide gel electrophoresis with SYBR Gold staining. The IQ-EX control template, a 7.5 kb plasmid DNA, was used as a positive control. The samples were labeled with TdT and hybridized to the array in a 49° C. rotating hybridization oven for 16 hours. Streptavidin phycoerythrin (SAPE), and then antibody staining was performed. The microarrays were processed in the GeneChip Fluidic Station and the GeneChip Scanner. Signal intensity data was output for all four nucleotides, permitting quantitative estimates of allelic contribution. The allelic contribution was assessed using the raw data from the individual signal intensities by deriving the ratio of expected allele (REA), which is the log ratio of the raw signal intensity of the expected allele at any site (as defined by the mtDNA reference sequence) to the average raw signal intensity of the other three alleles, at each site for every individual. DAT files with raw pixel data were generated and used as input for grid alignment. CEL files generated from DAT files were analyzed in batches using GSEQ. Samples with call rates of less than 95% were discarded. For samples passing initial filtering, ResqMi 1.2 50 was used for re-analysis of bases originally called as "N" by GSEQ. Analysis was performed using custom Perl scripts. Data was extracted from gene regions as defined by NCBI annotations for the revised Cambridge Reference Sequence (rCRS; NC 012920.1; incorporated herein by reference).

The MitoChip provides a quantitative output of signal intensity data for each nucleotide, allowing quantitative estimates of allelic contribution. Quantitative estimates of heteroplasmy were calculated with established methods that were previously used to assess heteroplasmy in the platelets of 19 AD patients and 18 matched controls. Briefly, heteroplasmy was derived for each mtDNA nucleotide by first calculating (a) the minor allele signal (MAS) defined as the raw signal intensity of the highest "non-expected" or minor allele minus the raw signal intensity value of the smallest contributing or background allele, and (b) the background subtracted expected allele signal (EAS) defined as the raw signal intensity of the expected allele (revised Cambridge Reference Sequence; NC_012920.1) minus the raw signal intensity of the smallest contributing or background allele. Percent heteroplasmy was then defined as MAS/(MAS+ EAS). The MitoChip has been shown to have a detection limit of 2% heteroplasmy and excluded from analysis were all loci with a calculated heteroplasmy value<2%. Twenty samples were repeated for concordance testing. Laboratory personnel were blinded to QC and case-control status and all 20 QC samples had >98% sequence concordance of nucleotide calls and the within-chip error rate was 0.0028%, which is comparable to previously published rates of 0.0025% and 0.0021%. The coefficient of variation (CV) values for the 20 repeated samples ranged from 14-27% for the seven complex I heteroplasmic mtDNA mutations (Table

TABLE 1

Mitochondrial heteroplasmy values for seven mitochondrial DNA (mtDNA) mutations related to complex I disease. mtDNA was collected and sequenced from platelets in year two of the Health, Aging, and Body Composition Study. Mean and standard deviation (SD) are adjusted for age and sex.

| mtDNA | Heteroplasmy | | |
|---|---|---|---|
| | Mean (SD) | Range | CV* |
| m.10158T > C | 0.12 (0.04) | (0.02-0.23) | 0.14 |
| m.10191T > C | 0.09 (0.03) | (0.02-0.18) | 0.27 |
| m.10197G > A | 0.05 (0.02) | (0.02-0.12) | 0.17 |
| m.13091T > C | 0.15 (0.03) | (0.08-0.23) | 0.14 |
| m.13513G > A | 0.16 (0.01) | (0.13-0.2) | 0.19 |
| m.13514A > G | 0.09 (0.03) | (0.03-0.18) | 0.20 |
| m.14487T > C | 0.26 (0.03) | (0.20-0.33) | 0.12 |

*Coefficient of variation (CV) values for 20 repeated DNA samples.

The information provided in the examples disclose various correlations between mitochondrial mutational and mitochondrial-associated disease(s) or condition(s), or predicting a predisposition for a mitochondrial-associated disease(s) or condition(s). For example, mtDNA heteroplasmy at particular nucleotide position(s) of the mitochondrial genome can be correlated with a decrease in performance on cognitive function tests. In this example the correlation of heteroplasmy with decreased performance on the test can be used to 1) confirm that decreased cognitive function is related to mitochondrial dysfunction and 2) provide a health care professional with the opportunity to prescribe medication that can address the disease or disorder. Alternatively, a subject may display heteroplasmy consistent with cognitive function impairment but the subject may not show a decrease in performance on a test that assesses cognitive function. In this case the subject may be placed on, for example, a pharmaceutical or dietary regimen specifically formulated to prevent or inhibit the onset of a cognitive disorder. In another example, a subject's mitochondrial heteroplasmic profile can be correlated with circulating amyloid beta (Aβ) levels. A subject identified as having a particular heteroplasmic profile and above-average levels of circulating AP can be predisposed to developing a neurological disorder such as AD. The subject may not, as of the time of testing, display a phenotype associated with AD (e.g., memory loss). However, a healthcare professional can use the information to generate, via methods and systems described herein, a personalized health plan designed to eliminate or mitigate the subject's risk of developing the neurological disorder. In another example, a subject can possess a mitochondrial heteroplasmic profile that identifies the subject as susceptible to developing sepsis. In this example the subject need not manifest any other phenotypic or genotypic characteristic in order for their heteroplasmic profile to be useful for a health care professional. For example, once the subjects profile is stored in a database or other electronic medium, the information is available to health care professionals that may treat the subject in the future. If, for example, the subject is scheduled to undergo a surgical procedure, or any procedure that raises the risk of developing an infection, the subject's heteroplasmic profile informs the health care professional that antibiotics should be administered prospectively in order to avoid the possibility of sepsis.

Cognitive Function Testing.

The Modified Mini-Mental State Examination (3MS) was administered to participants at year one (baseline) and year three. The 3MS is a brief, general cognitive battery with components for orientation, concentration, language, praxis, and immediate and delayed memory. Possible scores range from 0 to 100, with higher scores indicating better cognitive function.

Statistical Analyses.

Generalized linear models were used to analyze year three 3MS as the outcome and year two platelet mtDNA heteroplasmy at each of the seven complex I sites as the independent variables (m.10158T>C, m.10191T>C, m.10197G>A, m.13091T>C, m.13513G>A, m.13514A>G, m.14487T>C). For heteroplasmic mutations exhibiting a significant linear associations ($p<0.05$), year 3MS was compared among tertiles of heteroplasmy using $\chi^2$ tests. All analyses were adjusted for age, sex, clinic site, and year one 3MS score using SAS version 9.1 (SAS Institute Inc, Cary, N.C.).

A total of 132 Health ABC participants with year three 3MS and mtDNA heteroplasmy data were available for analysis. Of these, 61 were men and 71 were women, with a mean (SD) baseline age of 73.5 (2.9) years. Of the seven complex I candidate mtDNA mutations examined, heteroplasmy at the m.10158T>C, p.S34P, ND3 mutation was significantly associated with 3MS (p=0.009) and the effect was stronger than that observed for age (p=0.086). Heteroplasmy levels for m.10158T>C ranged from 2.0-23.0% and tertiles included 44 participants per group with the following ranges: low, 2.0-10.8%; middle, 10.8-13.4%; and high, 13.4-23.0%. When compared across tertiles of m.10158T>C heteroplasmy, mean (SE) 3MS was significantly lower (p=0.006) for the lowest tertile, 91.5 (0.83), when compared with the highest tertile, 94.7 (0.82), (FIG. 1).

Further, the mitochondrial DNA (mtDNA) m.15244A>G, p.G166G, CytB variant was found to be associated with a significant decline in cognitive function as measured by the Digit Symbol Substitution Test (β=−0.58, 95% confidence interval (CI) −0.89, −0.28, p=0.00019). In addition, the mtDNA m.14178T>C, p.I166V, ND6 variant was found to be associated with a significant decline in cognitive function as measured by The Modified Mini-Mental State Examination (β=−0.87, 95% CI −1.31, −3.86, p=0.00012).

Amyloid Beta (2β) Levels.

The mtDNA m.5046G>A, p.V193I, ND2 variant was found to be associated with significantly higher serum Aβ42 levels (p=0.0012). Carriers of the m.5046A allele have an elevated mean (SE) Aβ42 of 43.0 (3.5) pg/mL when compared with a mean (SE) Aβ42 of 31.2 (0.59) pg/mL for carriers of the m.5046G allele.

Peripheral Nerve Function.

The mtDNA m.1703C>T variant was found to be associated with significantly higher nerve conduction velocity (p=0.004). Carriers of the m.1703T allele have an elevated mean (SE) nerve conduction velocity of 53.9 (6.9) m/s when compared with a mean of 42.3 (0.88) m/s for carriers of the m.1703C allele. In addition, the mtDNA m.2850C>T variant was found to be associated with significantly higher nerve conduction velocity (p<0.001). Carriers of the m.2850C allele have an elevated mean (SE) nerve conduction velocity of 48.9 (4.9) m/s when compared with a mean of 42.4 (0.90) m/s for carriers of the m.2850T allele. Further, the mtDNA m.2639C>T variant was found to be associated with significantly higher nerve conduction velocity (p=0.004). Carriers of the m.2639T allele have an elevated mean (SE) nerve conduction velocity of 53.9 (6.9) m/s when compared with a mean of 42.3 (0.88) m/s for carriers of the m.2639C allele.

Kidney Function.

The mtDNA m.3915G>A, ND1 SNP is associated with significantly higher urinary KIM-1levels (p=1.2e-8). Carriers of the m.3915A allele have elevated mean (SE) KIM-1levels of 2599 (233) pg/ml when compared with a mean of 1207 (38) pg/ml for carriers of the m.3915G allele. In addition, the mtDNA m.10589G>A, ND4L SNP was associated with significantly lower urinary eGFR levels (p=0.0001). Carriers of the m.10589A allele have reduced mean (SE) eGFR levels of 57.3 (5.2) ml/minute/1.73 m2 when compared with a mean of 70.8 (0.44) ml/minute/1.73 m2 for carriers of the m.10589G allele. Further, the mtDNA m.10589G>A, ND4L SNP was associated with significantly higher urinary KIM-1levels (p=0.0001). Carriers of the m.10589A allele have elevated mean (SE) KIM-1levels of 3000 (444) pg/ml when compared with a mean of 1232 (38) pg/ml for carriers of the m.10589G allele. Finally, the mtDNA m.15758A>G, CYTB SNP was associated with significantly higher urinary KIM-1levels (p=0.0001). Carriers of the m.15758A>G allele have elevated mean (SE) KIM-1levels of 3476 (513) pg/ml when compared with a mean of 1074 (46) pg/ml for carriers of the m.15758A allele.

Relatedly, the mtDNA m.6776T>C, COI SNP was found to be associated with significantly higher urinary albumin/creatinine ratio (p=8.0e-5). Carriers of the m.6776C allele have elevated mean urinary albumin/creatinine ratios 98.1 (16.5) when compared with a mean of 28.9 (3.9) for carriers of the m.6776T allele.

Septic Mortality.

The mtDNA m.3918G>A SNP was found to be associated with significantly higher risk of mortality from sepsis (p=0.05). Carriers of the m.3918A allele have elevated risk of septic mortality (Hazard Ratio (HR)=2.2; 95% CI=1.0-4.6) when compared with carriers of the m.3918G allele. In addition, the mtDNA m.6152T>C SNP was associated with significantly higher risk of mortality from sepsis (p=0.05). Carriers of the m.6152C allele have elevated risk of septic mortality (HR=4.3; 95% CI=1.0-19.2) when compared with carriers of the m.6152T allele. Further, the mtDNA m.11899T>C SNP was associated with significantly higher risk of mortality from sepsis (p=0.05). Carriers of the m.11899C allele have elevated risk of septic mortality (HR=4.7; 95% CI=1.5-14.9) when compared with carriers of the m.11899T allele. Finally, the mtDNA m.15244A>G SNP was associated with significantly higher risk of mortality from sepsis (p=0.05). Carriers of the m.15244G allele have elevated risk of septic mortality (HR=2.1; 95% CI=1.0-4.7) when compared with carriers of the m.15244A allele.

Heteroplasmy and Vision.

Figure 5:
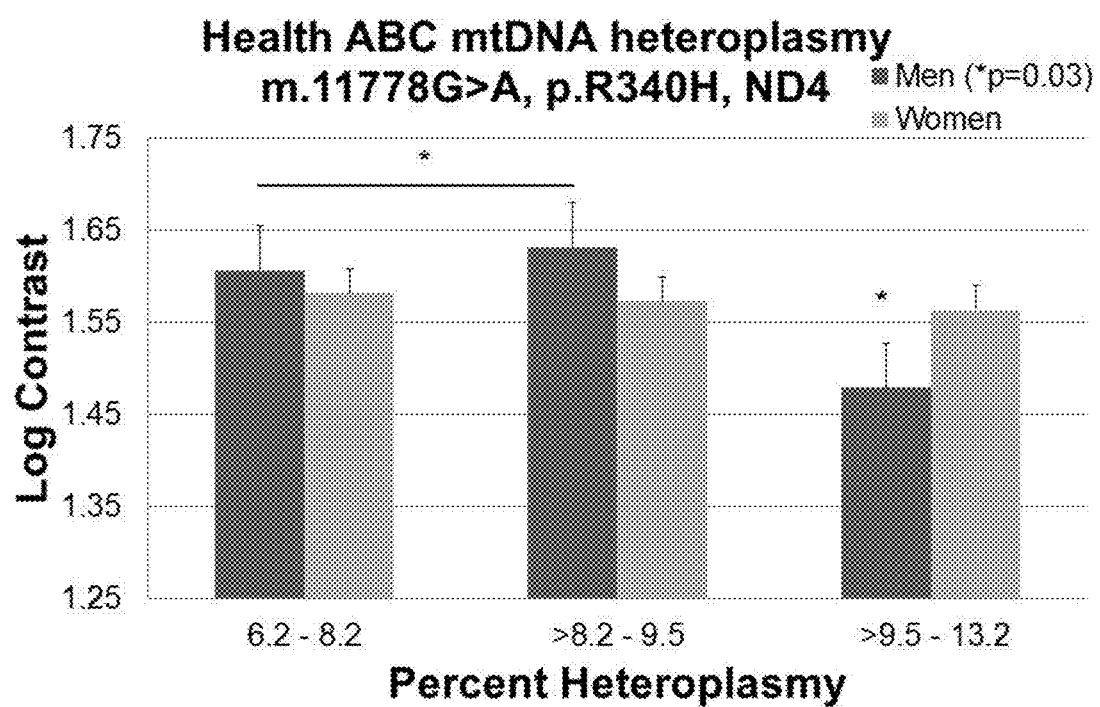
FIG. 5 shows mitochondrial m.11778G>A heteroplasmy and visual contrast sensitivity.

Of the three Leber's hereditary optic neuropathy (LHON) mutations examined for effects on vision, increased heteroplasmy at m.11778G>A (n=133) was significantly associated with decreased contrast sensitivity (p=0.02), a measure of retinal function. Mean (SE) log contrast was significantly poorer for participants in the highest tertile of heteroplasmy, 1.53 (0.03) when compared with those in the middle, 1.60 (0.03), p=0.04; lowest, 1.60 (0.03), p=0.03; and the combined middle and lowest tertiles, 1.60 (0.03), p=0.034. The primary LHON mutations exhibit a higher penetrance in men than women and the present data indicates that the impact of m.11778G>A heteroplasmy was stronger in male (p=0.045) than female (p=0.32) participants (FIG. 5). Men in the highest tertile of heteroplasmy exhibited significantly lower mean (SE) log contrast, 1.49 (0.05) when compared with those in the middle, 1.59 (0.05), p=0.04; lowest, 1.65 (0.06), p=0.03; and the combined middle and lowest tertiles, 1.62 (0.05), p=0.03. The remaining candidate LHON mutations did not appear to be associated with visual contrast sensitivity and no associations were identified for distance visual acuity or stereo test.

The present results also demonstrate that elevated levels of the m.11778G>A, p.R340H, ND4 (NADH dehydrogenase 4) substitution in Complex I were associated with significantly decreased contrast sensitivity. For example, the data indicate that m.11778G>A heteroplasmy impacted contrast sensitivity above the 9.5% mutation burden threshold.

This result provides support for the observation that asymptomatic m.11778G>A LHON mutation carriers experience progressive subclinical retinal ganglion cell dysfunction that eventually leads to permanent ganglion cell loss and subsequent blindness. The three primary Complex I subunit LHON mutations (including m.11778G>A which accounts for up to 70% of LHON cases have been extensively investigated using a wide range of cell types and biochemical assays. Cybrid studies support the present data by demonstrating that carriers of either one of the three most common primary LHON mutations exhibit elevated ROS levels, decreased mitochondrial membrane potential, impaired complex I-dependent ATP synthesis, hyper-fragmented mitochondrial networks, and increased rates of apoptotic cell death.

Two characteristics of LHON include incomplete penetrance of mutations and the significant male bias in disease predisposition. Overall, 50% of male LHON mutation carriers and 10% of female mutation carriers eventually lose vision. The present data indicate that the effect of m.11778G>A heteroplasmy on age-related contrast sensitivity was stronger in men than women, largely resembling the m.11778G>A LHON association pattern. This disparity can be in part be explained by hormonal influence or additional genetic factors involving interactions with the X-chromosome or mitochondrial haplogroup. Supplementation of cybrids carrying of LHON mutations with 17b-estradiol mitigates many pathological features (e.g. elevated ROS levels and increased apoptosis) (Brain. 2011; 134:220-234). This hormone treatment leads to more efficient mitochondrial biogenesis and an increase in cellular levels of the anti-oxidant enzyme superoxide dismutase (SOD) which protects LHON cells against enhanced superoxide production by mutated complex I.

Table 2 provides a list of mitochondrial associated diseases and disorders and the polymorphic mtDNA sites:

Pathogenic mtDNA mutations for various diseases and phenotypic presentations.

| CARDIO-MYOPATHY | DEAFNESS/SENSORI-NEURAL HEARING LOSS | DIABETES MELLITUS | ENCEPHALO-MYOPATHY | MITO-CHONDRIAL MYOPATHY | | LEIBER'S HEREDITARY OPTIC NEURO-PATHY | LEIGH SYNDROME/DYSTONIA | ALZHEIMER'S/DEMENTIA/PARKINSON'S |
|---|---|---|---|---|---|---|---|---|
| A3260G | C1494T | A3243G | G583A | T7512C | A3243G | G12207A | G11778A | T8993C | G3196A |
| C3303T | A1555G | C1310T | G1606A | G8328A | A3302G | C3303T | G3460A | T8993G | T4336C |
| A4300G | A7445G | A1438G | A3243G | A8332G | G4298A | A5843G | T14484C | T9176G | G5549A |
| A4295G | T7511C | T3264C | C3256T | T10010C | G4308A | A8326G | G3635A | T9176C | A3397G |
| A4300G | A636G | T3271C | T3271C | A10438G | G5650A | G15995A | G3700A | T9185C | G5460A |
| C5545T | A827G | T4291C | T3291C | C14680A | G5703A | A15923G | G3733A | T10158C | G5460T |
| A8348G | T961C | A8296G | G4332A | A14696G | G7497A | G8313A | C4171A | T10191C | |
| T9997C | T961delT + C(n)ins | C12258A | A5537insT | G14724A | G12315A | A10006G | T10663C | G10197A | |
| G12192A | | A12026G | C7472insC | G14740A | T14674C | C12246G | G14459A | C11777A | |
| T12297C | T961insC | | A8344G | G15915A | T14709C | A606G | C14482A | T12706C | |
| A4269G | T1005C | | T8356C | T582C | A608G | C3254T | C14482G | G14459A | |
| A4317G | A1116G | | G8363A | C15975T | T618C | C3254T | A14495G | T14487C | |
| G15243A | C1494T | | T10010C | C2835T | G622A | T4274C | T14502C | A3796G | |
| G15498A | G5783A | | G12147A | G4284A | T642C | T4285C | C14568T | T9176C | |
| T6721C | T7510C | | C1624T | A10044G | G3242A | G4298A | | T9176G | |
| T6742C | T7511C | | G1644T | T3308C | T3250C | G4309A | | T9185C | |
| | 7472insC | | A5537insT | G3376A | A3251G | T5628C | | T9191C | |
| | G12183A | | G611A | G3697A | C3254G | T5692C | | C9537insC | |
| | T14709C | | G8361A | G3946A | A3280G | G5698A | | T1659C | |
| | A7443G | | G8363A | T3949C | A3288G | G5703G | | | |
| | A7445C | | G3255A | A11084G | A4267G | G8342A | | | |
| | G7444A | | A7543G | A12770G | A4302G | G12294A | | | |
| | A8108G | | G1606A | A13045C | T4370AT | T12311C | | | |
| | C14340T | | G3244A | A13084T | T4409C | G12315A | | | |
| | | | A3252G | G14453A | G4450A | T15940G | | | |

-continued

Pathogenic mtDNA mutations for various diseases and phenotypic presentations.

| CARDIO-MYOPATHY | DEAFNESS/ SENSORI-NEURAL HEARING LOSS | DIABETES MELLITUS | ENCEPHALO-MYOPATHY | MITO-CHONDRIAL MYOPATHY | | LEIBER'S HEREDI-TARY OPTIC NEURO-PATHY | LEIGH SYNDROME/ DYSTONIA | ALZ-HEIMER'S/ DEMENTIA/ PARKIN-SON'S |
|---|---|---|---|---|---|---|---|---|
| | | | T3258C | 14787del4 | G5521A | G5532A | | |
| | | | T3291C | C6489A | T5543C | G3249A | | |
| | | | G1642A | G6930A | T5543C | T3273C | | |
| | | | G583A | 6015del5 | T5567C | G14846A | | |
| | | | C3093G | T7587C | G5591A | G15059A | | |
| | | | T3271delT | G7896A | T5636C | G15084A | | |
| | | | C287A | 8042del2 | G7458A | G15150A | | |
| | | | T4290C | G9952A | T7480G | G15168A | | |
| | | | C4320T | T9957C | G7497A | T15197C | | |
| | | | G5540A | 9205del2 | A7526G | G15242A | | |
| | | | T5693C | A15579G | T8355C | G15497A | | |
| | | | T5814C | T14849C | T8362G | 15498del24 | | |
| | | | A5816G | T5728C | G10406A | G15615A | | |
| | | | | | G12316A | G15723A | | |
| | | | | | A12320G | G15762A | | |
| | | | | | T14674G | T11232C | | |
| | | | | | A14687G | G11832A | | |
| | | | | | T14723C | G5920A | | |
| | | | | | G14739A | G6708A | | |
| | | | | | T15940delT | T7671A | | |
| | | | | | C15990T | T7989C | | |
| | | | | | T16002C | 9487del15 | | |

Table 3 provides a list of aging traits that can be identified by the methods and compositions of the disclosure:

TABLE 3

Aging traits and diseases to be assessed for mtDNA mutation (heteroplasmy) associations.

| AGING TRAITS | DISEASES |
|---|---|
| Arterial stiffness | Osteoarthritis |
| Blood pressure | Cardiovascular Disease: |
| Hearing acuity | myocardial infarction, angina, CHF, |
| Metabolic rate | intermittent claudication, CABG, |
| Body composition: | valvular heart disease, hypertension |
| BMI, weight, intramsucular fat, obesity | heart attack, angina. |
| Mobility: | Pulmonary: |
| walking speed, balance | pneumonia, COPD, emphysema |
| Muscle strength | chronic bronchitis, asthma |
| Peripheral neuropathy | Peripheral vascular disease |
| Pulmonary function | Stroke |
| Pulse | TIA |
| Respiratory function: | Congestive heart failure |
| Arrhythmia, Tachycardia, Bradycardia | Hypertension |
| Olfaction | Diabetes |
| Vision: | Osteoporosis |
| visual acuity, distance, stereo vision, | Fractures |
| contrast sensitivity | Falls |
| Cognitive function: | Neuropathy |
| CLOX 1, Digit Symbol Substitution test, | Parkinson's |
| Exit 15, Teng Mini-Mental State Exam, | Alzheimer's |
| Cognitive Vitality, Buschke Selective reminder test, | Depression |
| Boxes test, Digit copying test, | Cancer |
| Pattern comparison test, | Hypothyroidism/hyperthyroidism |
| Letter comparison test, Simple reaction time test, | Ulcer |
| Digit Symbol test | Sepsis |
| Dental caries | Gallstones |

TABLE 3-continued

Aging traits and diseases to be assessed for mtDNA mutation (heteroplasmy) associations.

| AGING TRAITS | DISEASES |
|---|---|
| Insulin levels | Gout |
| Glucose levels | Kidney disease |
| | Shingles |

A number of embodiments have been described herein. Nevertheless, it will be understood that various modifications may be made without departing from the spirit and scope of this disclosure. Accordingly, other embodiments are within the scope of the following claims.

What is claimed is:

1. A method comprising:
   (a) isolating mtDNA from a platelet sample obtained form a subject who is at least 65 years old;
   (b) measuring a heteroplasmy at position 11778 of the mtDNA by using a hybridization assay or by using a sequencing assay, wherein the heteroplasmy is the result of accumulation of somatic mtDNA mutations at position 11778 over the subject's lifetime;
   (c) determining the frequency of 11778A to 11778G;
   (d) detecting a frequency of 11778A of greater than 9.5% of the total number of alleles (11778A+11778G);
   (e) diagnosing the subject as being at risk for clinically significant vision loss as measured by contrast sensitivity testing; and
   (f) administering to the diagnosed subject rapamycin and/or 17b-estradiol.

2. A method comprising:
   determining by a hybridization assay or by sequencing the presence and frequency of a mutation in a nucleic acid sequence encoding at least one subunit of mitochondrial complex I (mtDNA) having an m.11778G>A, in a platelet sample obtained from a subject who is at least 65 years old, detecting a frequency of 11778A that is greater than 9.5% of the total number of alleles (11778A+11778G), then diagnosing the subject as being at risk for clinically significant vision loss as measured by contrast sensitivity testing; and administering to the diagnosed subject rapamycin and/or 17b-estradiol.

3. The method of claim 1 or 2, wherein the mtDNA is isolated from a mitotic or post-mitotic cell population.

* * * * *